United States Patent
Alary et al.

(10) Patent No.: US 11,413,440 B2
(45) Date of Patent: *Aug. 16, 2022

(54) THREE-DIMENSIONAL MICROFLUIDICS DEVICES FOR THE DELIVERY OF ACTIVES

(71) Applicant: Johnson & Johnson Consumer Inc., Skillman, NJ (US)

(72) Inventors: Marc Alary, Skillman, NJ (US); Bharat Patel, Skillman, NJ (US); Peyton Hopson, Jacksonville, FL (US); Jan-Joo Liu, Skillman, NJ (US); Vipul Davé, Hillsborough, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 500 days.

This patent is subject to a terminal disclaimer.

(21) Appl. No.: 16/457,125

(22) Filed: Jun. 28, 2019

(65) Prior Publication Data
US 2020/0001065 A1  Jan. 2, 2020

Related U.S. Application Data

(60) Provisional application No. 62/691,699, filed on Jun. 29, 2018.

(51) Int. Cl.
*A61M 37/00* (2006.01)
*B33Y 80/00* (2015.01)
(Continued)

(52) U.S. Cl.
CPC ....... *A61M 37/0015* (2013.01); *A61K 9/0021* (2013.01); *A61K 31/135* (2013.01);
(Continued)

(58) Field of Classification Search
CPC ...... A61M 37/0015; A61M 2037/0053; A61M 2205/3379; A61M 2037/0023;
(Continued)

(56) References Cited

U.S. PATENT DOCUMENTS 6,611,707 B1 * 8/2003 Prausnitz .......... A61M 37/0015
604/21
6,623,457 B1    9/2003 Rosenberg
(Continued)

FOREIGN PATENT DOCUMENTS

CN    105126243 A    12/2015
CN    204890945 U    12/2015
(Continued)

OTHER PUBLICATIONS

International search report and written opinion dated Jan. 3, 2020, for international application PCT/IB2019/055530.
(Continued)

*Primary Examiner* — Amber R Stiles

(57) ABSTRACT

A transdermal delivery device includes a film having first and second outwardly facing major surfaces; at least one liquid reservoir contained within the film; at least one microfluidic channel having a transverse dimension between about 100 nm and 0.5 mm disposed within the film and in fluid communication with the at least one liquid reservoir; and at least one outlet port associated with at least one microneedle operatively connected to the first outwardly facing major surface of the film in fluid communication with the at least one microfluidic channel.

16 Claims, 6 Drawing Sheets

(51) Int. Cl.
*A61K 9/00* (2006.01)
*A61K 31/135* (2006.01)
*A61K 31/167* (2006.01)
*A61K 31/192* (2006.01)
*A61K 31/485* (2006.01)
*A61K 31/4965* (2006.01)

(52) U.S. Cl.
CPC .......... *A61K 31/167* (2013.01); *A61K 31/192* (2013.01); *A61K 31/485* (2013.01); *A61K 31/4965* (2013.01); *B33Y 80/00* (2014.12); *A61M 2037/003* (2013.01); *A61M 2037/0023* (2013.01); *A61M 2037/0053* (2013.01); *A61M 2205/3327* (2013.01); *A61M 2205/3379* (2013.01)

(58) Field of Classification Search
CPC .... A61M 2037/003; A61M 2205/3327; B33Y 80/00; A61K 9/0021; A61K 31/135; A61K 31/167; A61K 31/192; A61K 31/485; A61K 31/4965; A61K 45/06; A61K 9/7092; A61K 9/0014; A61K 9/70
See application file for complete search history.

(56) References Cited

U.S. PATENT DOCUMENTS

| | | | |
|---|---|---|---|
| 7,030,411 B2 | 4/2006 | Krulevitch et al. | |
| 7,540,717 B2 | 6/2009 | Sheng et al. | |
| 8,343,425 B1 | 1/2013 | Li et al. | |
| 8,956,637 B2 | 2/2015 | Dubrow et al. | |
| 9,060,842 B2 | 6/2015 | Karp et al. | |
| 2002/0082307 A1* | 6/2002 | Dobrozsi | A61P 11/14 514/772 |
| 2003/0083645 A1 | 5/2003 | Angel et al. | |
| 2004/0121528 A1 | 6/2004 | Krulevitch et al. | |
| 2004/0267205 A1 | 12/2004 | Stemme et al. | |
| 2007/0078414 A1 | 4/2007 | McAllister et al. | |
| 2008/0183144 A1 | 7/2008 | Trautman | |
| 2009/0182306 A1 | 7/2009 | Lee et al. | |
| 2010/0221314 A1 | 9/2010 | Matsudo et al. | |
| 2010/0228203 A1 | 9/2010 | Quan et al. | |
| 2011/0028905 A1 | 2/2011 | Takada | |
| 2011/0087195 A1 | 4/2011 | Uhland et al. | |
| 2011/0244010 A1 | 10/2011 | Doshi | |
| 2012/0052234 A1 | 3/2012 | Natarajan et al. | |
| 2012/0220980 A1 | 8/2012 | Ross | |
| 2012/0265145 A1 | 10/2012 | Mefti et al. | |
| 2013/0116523 A1 | 5/2013 | Jung et al. | |
| 2014/0005606 A1 | 1/2014 | Chen et al. | |
| 2014/0081295 A1 | 3/2014 | Lau et al. | |
| 2014/0363610 A1 | 12/2014 | Sameoto | |
| 2015/0030642 A1 | 1/2015 | Wu et al. | |
| 2015/0141895 A1 | 5/2015 | Tuma | |
| 2015/0144259 A1 | 5/2015 | Laulicht et al. | |
| 2015/0329743 A1 | 11/2015 | Lu et al. | |
| 2015/0335872 A1 | 11/2015 | Yang et al. | |
| 2015/0352777 A1 | 12/2015 | DeSimone et al. | |
| 2016/0051195 A1 | 2/2016 | Pang et al. | |
| 2016/0296149 A1 | 10/2016 | Polsky et al. | |
| 2016/0346466 A1* | 12/2016 | Wang | A61M 37/0015 |
| 2017/0341075 A1 | 11/2017 | Sirkis et al. | |
| 2018/0177990 A1 | 6/2018 | Alary et al. | |
| 2018/0311486 A1 | 11/2018 | Park | |
| 2020/0001064 A1* | 1/2020 | Alary | A61K 9/0014 |

FOREIGN PATENT DOCUMENTS

| | | |
|---|---|---|
| EP | 1086718 A | 3/2001 |
| EP | 1699403 B | 9/2006 |
| EP | 2125608 B | 12/2009 |
| EP | 2548608 A | 1/2013 |
| JP | 2007089792 A | 4/2007 |
| JP | 2010069242 A | 4/2010 |
| JP | 2010069253 A | 4/2010 |
| JP | 2010233673 A | 10/2010 |
| JP | 2016171888 A | 9/2013 |
| JP | 2015226649 A | 12/2015 |
| KR | 20160121370 A | 10/2016 |
| WO | WO 2003/066126 A | 8/2003 |
| WO | WO 2005/103303 A | 11/2005 |
| WO | WO 2009/081122 A | 7/2009 |
| WO | WO 2010/022252 A | 2/2010 |
| WO | WO 2013/131215 A | 9/2013 |
| WO | WO 2014/142135 A | 9/2014 |
| WO | WO 2015/167991 A | 11/2015 |
| WO | WO 2016/052818 A | 4/2016 |

OTHER PUBLICATIONS

International search report and written opinion dated Dec. 19, 2019, for international application PCT/IB2019/055531.

* cited by examiner

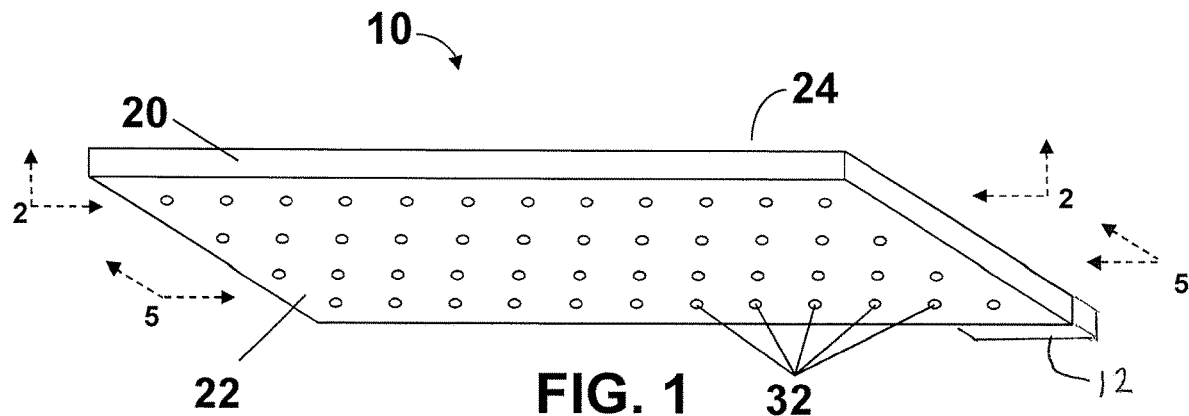
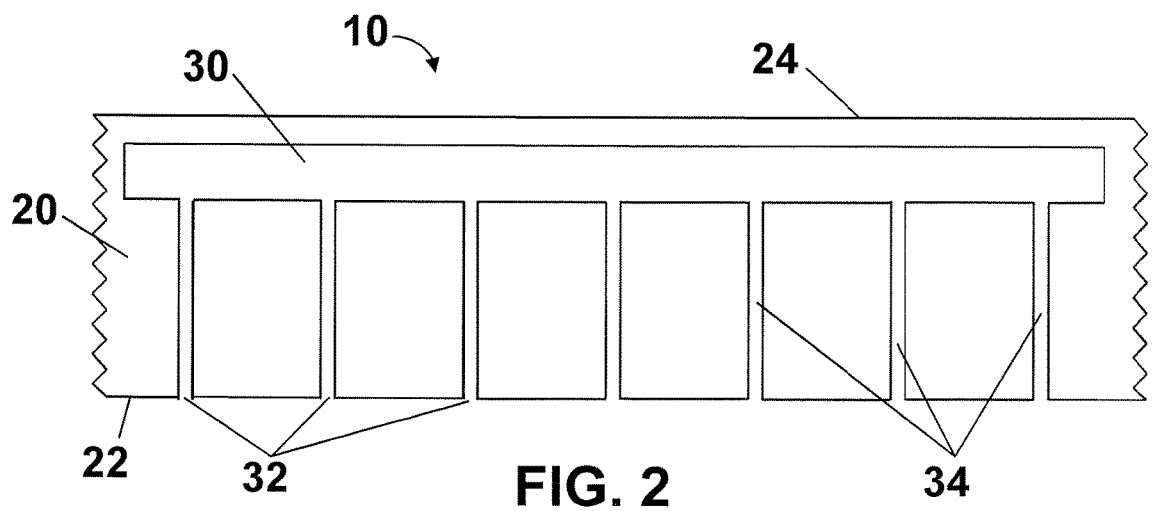
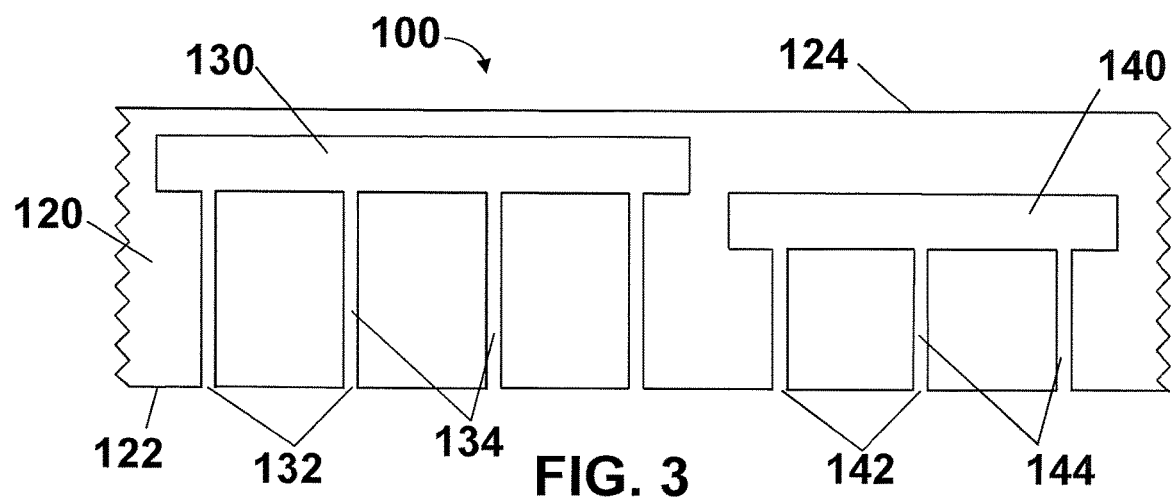

THREE-DIMENSIONAL MICROFLUIDICS DEVICES FOR THE DELIVERY OF ACTIVES

CROSS-REFERENCE TO RELATED APPLICATIONS

This application claims the benefit of U.S. provisional application 62/691,699 filed on Jun. 29, 2018.

FIELD OF THE INVENTION

The present invention relates to devices for the administration of benefit agents to patients at surface of the skin. More particularly, this invention relates to microfluidic devices comprising one or more benefit agents, and methods for making and using these devices.

BACKGROUND OF THE INVENTION

Dermal delivery refers to the process of mass transport of benefit agents applied on the skin to various skin strata. The application of benefit agents to the skin has a long history. Numerous carriers, including conventional semisolid bases (creams, gels, ointments), matrix systems (clays, polymers), and liquid systems (solutions, emulsions, suspensions), are being used for cutaneous application of benefit agents.

The human skin functions as the primary barrier to the transdermal penetration of materials into the body. Transdermal delivery refers to the process of mass transport of substances applied on the skin surface and includes their absorption by each layer of the skin, their uptake by microcirculation of the skin, and distribution in the systemic circulation. Transdermal delivery of benefit agents to patients through the skin provides many advantages over other means of delivery. Primarily, transdermal delivery is a comfortable, convenient and noninvasive way of administering benefit agents. Transdermal delivery also provides other advantages over other routes for administering a benefit agent formulation to a patient. For example, oral administration of some benefit agents may be ineffective because the benefit agent is destroyed in the gastrointestinal tract or eliminated by the liver, both of which are avoided by transdermal drug delivery. Parenteral injection with a conventional hypodermic needle also has drawbacks, as it is often painful and inconvenient. Transdermal benefit agent delivery also makes possible a high degree of control over blood concentrations of any agent.

Dermal and transdermal delivery may be accomplished by rubbing benefit agents onto the skin surface. But control of the amount and location of the benefit agent is an issue. Dermal and transdermal devices, also known as patches, are known for use in dermal and transdermal delivery of benefit agents. A delivery patch is a medicated adhesive patch that is placed on the skin to deliver a specific dose of medication to the surface of the skin. These patches are typically constructed of a backing layer and an adhesive layer. Often, the benefit agents (drugs, medications) are located in the adhesive layer, but may be located on the surface of the adhesive, or in a separate layer or reservoir. Benefit agents are released from the patch through the adhesive, or through porous membrane covering a reservoir.

Recently developed are patches which use microfluidic delivery to the skin surface. Microfluidics is the science dealing with the behavior, precise control, and manipulation of fluids that are geometrically constrained to a small, typically sub-millimeter, scale, and with very small volumes (such as nanoliters or picoliters).

Microfluidic devices move, mix, separate or otherwise process fluid. Numerous applications employ passive fluid control techniques like capillary forces. In some applications, external actuation means are used for a directed transport of the fluid. These include components such as micropumps or microvalves. Micropumps supply fluids in a continuous manner or are used for dosing. Microvalves determine the flow direction or the mode of movement of pumped liquids.

The main disadvantage to transdermal delivery systems stems from the fact that the skin is a very effective barrier; as a result, only medications whose molecules are small enough to penetrate the skin can be delivered by this method. A wide variety of benefit agents are now available in transdermal patch form.

To address the challenge of intact skin, a variety of microneedle-array based drug delivery devices have been developed. These known microneedle (or microprotrusions) arrays generally fall into one of two design categories: (1) solid microneedles arrays with no active component, and (2) microneedles with a central hollow bore, which are like conventional hypodermic needle.

Solid delivery devices can pre-condition the skin by piercing the stratum corneum and the upper layer of epidermis to enhance percutaneous drug penetration prior to topical application of a biologic-carrier or a traditional patch. If solid delivery devices are kept in the skin, then the drug cannot readily flow into and through the holes in the skin because the holes remain plugged by the microneedles. This method has been shown to significantly increase the skin's permeability; however, this method provides only limited ability to control the dosage and quantity of delivered drugs or vaccine.

To increase the dosage control some methods uses solid microneedles that are surface-coated with a drug, or solid microneedles that are biodegradable, bioabsorbable, or dissolvable. Although these methods provide a somewhat better dosage control, they greatly limit the quantity of drug delivered. Also, the drug formulation could be easily chipped off the microneedle during storage, transport, or administration (insertion) of the microneedles. The application of a thicker and stronger layer of drug formulation can be undesirable because it reduced the sharpness of the microneedles and therefore made insertion more difficult and painful. This shortcoming has limited the widespread application of these approaches and precludes, for example, the simultaneous delivery of optimal quantities of combinations of antigens and/or adjuvant in vaccine applications.

Microneedles with hollow bore attached to a reservoir of benefit agents are also known. The syringe needle-type characteristics of these arrays can significantly increase the speed and precision of delivery, as well as the quantity of the delivered agent. However, reservoir-based delivery devices are expensive to make and require complex and expensive micromachining procedures. It is difficult to make sharp tips on hollow microneedles with machining techniques. Consequently, insertion of the microneedles into a patient's skin can be difficult and often painful.

Dermal or transdermal delivery of benefit agents using patch devices offer attractive theoretical advantages over other delivery methods. However, considerable practical limitations exist in the design, fabrication, and testing associated with patches constructed using conventional processes. Also, there is a need for a simple, effective, and economically desirable device for dermal or transdermal administration of using patches simultaneously delivering more than one benefit agent.

SUMMARY OF THE INVENTION

One aspect of the invention relates to a dermal delivery device comprising:
- (a) film having first and second outwardly facing major surfaces;
- (b) at least one liquid reservoir contained within the film;
- (c) at least one microfluidic channel having a transverse dimension between about 100 nm and 0.5 mm disposed within the film and in fluid communication with the at least one liquid reservoir;
- (d) at least one outlet port operatively connected to the first outwardly facing major surface of the film in fluid communication with the at least one microfluidic channel.

Another aspect of the invention relates to a dermal delivery device comprising:
- (a) film having first and second outwardly facing major surfaces;
- (b) a plurality of liquid reservoirs contained within the film;
- (c) each liquid reservoir being in fluid communication with at least one microfluidic channel having a major transverse dimension between about 100 nm and 0.5 mm disposed within the film;
- (d) at least one outlet port operatively connected to the first outwardly facing major surface of the film in fluid communication with at least one microfluidic channel.

A third aspect of the invention relates to a transdermal delivery device comprising:
- (a) film having first and second outwardly facing major surfaces;
- (b) at least one liquid reservoir contained within the film;
- (c) at least one microfluidic channel (having a major transverse dimension between about 100 nm and 0.5 mm) disposed within the film and in fluid communication with the at least one liquid reservoir;
- (d) at least one outlet port operatively connected to the first outwardly facing major surface of the film in fluid communication with the at least one microfluidic channel;
- (e) at least one microneedle in fluid communication with the at least one outlet port.

BRIEF DESCRIPTION OF THE DRAWINGS

FIG. 1 is a perspective view of a first embodiment microfluidic delivery device of the present invention;

FIG. 2 is a cross-sectional view of a section of the microfluidic delivery device of FIG. 1 along the 2-2 plane;

FIG. 3 is a cross-sectional view of a second embodiment of the microfluidic delivery device of FIG. 1 along the 2-2 plane;

DETAILED DESCRIPTION OF THE INVENTION

Figure 4:
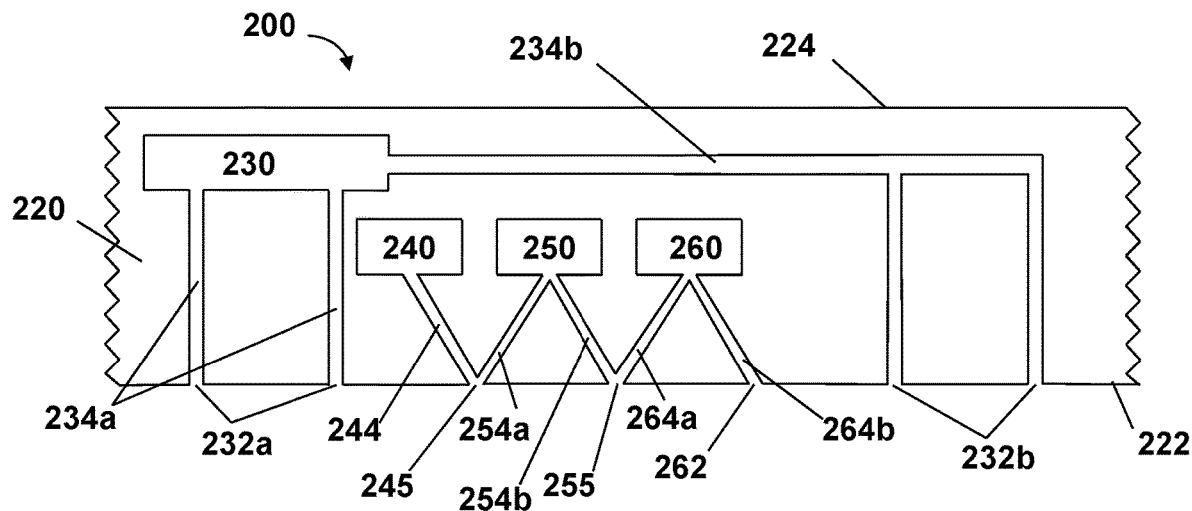
FIG. 4 is a cross-sectional view of a third embodiment of the microfluidic delivery device of FIG. 1 along the 2-2 plane.

The present invention relates to devices for the dermal or transdermal administration of a plurality of benefit agents to patients using microfluidic delivery devices, and methods for making and employing these devices.

The presently disclosed subject matter will now be described more fully hereinafter with reference to the accompanying drawings and examples, in which representative embodiments are shown. The presently disclosed subject matter can, however, be embodied in different forms and should not be construed as limited to the embodiments set forth herein, but is to be accorded the widest scope consistent with the features described herein. Rather, these embodiments are provided so that this disclosure will be thorough and complete, and will fully convey the scope of the embodiments to those skilled in the art. Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

As used herein the specification and the claims, the term "topical" and variants thereof mean "of or applied to an isolated part of the body". This includes, without limitation skin, mucosa, and enamel, either directly or through an intermediate such as a biofilm.

As used herein, "benefit agent" means an ingredient or material that provides a benefit, e.g., improves, relieves, reduces, or treats symptoms or conditions of the skin or body, either cosmetic or therapeutic. Other terms of use for "benefit agent" include "biologic," "active component," "active formulation," or "bioactive material". These terms all refer to pharmaceutically active agents, such as analgesic agents, anesthetic agents, anti-asthmatic agents, antibiotics, anti-depressant agents, anti-diabetic agents, anti-fungal agents, anti-hypertensive agents, anti-inflammatory agents, anti-neoplastic agents, anxiolytic agents, enzymatically active agents, nucleic acid constructs, immunostimulating agents, immunosuppressive agents, vaccines, and the like. The benefit agent material can comprise dissoluble materials, insoluble but dispersible materials, natural or formulated macro, micro and nano particulates, and/or mixtures of two or more of dissoluble, dispersible insoluble materials and natural and/or formulated macro, micro and nano particulates.

As used herein, the term "microfluidic delivery device" generally refers to a device through which materials, particularly fluid borne materials, such as liquids, can be transported, in some embodiments on a micro-scale, and in some embodiments on a nano-scale. Thus, the microfluidic devices described by the presently disclosed subject matter can include microscale features, nanoscale features, and/or combinations thereof.

Accordingly, a microfluidic device typically includes structural or functional features dimensioned on the order of a millimeter-scale or less, which are capable of manipulating a fluid at a flow rate on the order of a microliter/min or less. Typically, such features include, but are not limited to channels, fluid reservoirs, reaction chambers, mixing chambers, and separation regions. In some examples, the channels having at least one transverse dimension between about 100 nanometers and about 0.5 millimeter (about 500 micrometers). The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., reagents, buffers and the like, into the system and/or through the system; detection equipment or systems; reagent, product or data storage systems; and control systems for controlling fluid transport and/or direction within the device, monitoring and controlling environmental conditions to which fluids in the device are subjected, e.g., temperature, current, and the like.

As used herein, the terms "channel," "microscale channel," and "microfluidic channel" are used interchangeably and can mean a recess or cavity formed in a material, or can mean a recess or cavity in combination with any suitable fluid-conducting structure mounted in the recess or cavity, such as a tube, capillary, or the like. The terms "flow channel" and "control channel" are used interchangeably and can mean a channel in a microfluidic device in which a material, such as a fluid, e.g., a liquid, can flow through. More particularly, the term "flow channel" refers to a channel in which a material of interest can flow through. More particularly, such a channel is filled with a fluid that does not permeate the material of the microfluidic device As used herein, the term "valve" unless otherwise indicated refers to a configuration in which two channels are separated by an elastomeric segment that can be deflected into or retracted from one of the channels, e.g., a flow channel, in response to an actuation force applied to the other channel, e.g., a control channel. The term "valve" also includes one-way valves, which include channels separated by a bead.

As used herein, the term "pattern" can mean a channel or a microfluidic channel or an integrated network of microfluidic channels, which, in some embodiments, can intersect at predetermined points. A pattern also can include one or more of a fluid reservoir, or micro- or nano-scale fluid reservoir, a micro- or nano-scale reaction chamber, a micro- or nano-scale mixing chamber, a micro- or nano-scale separation region, a surface texture, a pattern on a surface that can include micro and/or nano recesses and/or projections. The surface pattern can be regular or irregular.

As used herein, the term "intersect" can mean to meet at a point, to meet at a point and cut through or across, or to meet at a point and overlap. More particularly, as used herein, the term "intersect" describes an embodiment wherein two or more channels meet at a point, meet at a point and cut through or across one another, or meet at a point and overlap one another. Accordingly, in some embodiments, two channels can intersect, i.e., meet at a point or meet at a point and cut through one another, and be in fluid communication with one another. In some embodiments, two channels can intersect, i.e., meet at a point and overlap one another, and not be in fluid communication with one another, as is the case when a flow channel and a control channel intersect.

As used herein, the term "communicate" (e.g., a first component "communicates with" or "is in communication with" a second component) and grammatical variations thereof are used to indicate a structural, functional, mechanical, electrical, optical, or fluidic relationship, or any combination thereof, between two or more components or elements. As such, the fact that one component is said to communicate with a second component is not intended to exclude the possibility that additional components can be present between, and/or operatively associated or engaged with, the first and second components.

In referring to the use of a microfluidic device for handling the containment or movement of fluid, the terms "in", "on", "into", "onto", "through", and "across" the device generally have equivalent meanings. As used herein, the term "monolithic" refers to a structure having or acting as a single, uniform structure.

In some embodiments, the microfluidic delivery device may be more rigid; built as the described three-dimensional shape to match the topical contour. The delivery device may have varying personalized area-specific treatment zones to enable the treatment application more effectively. With a design matched to the individual user's body part profile as physical guides, the application becomes easier and more effective, and can help in locating specific target zones to the precise area for applications.

Referring to the drawings, FIG. 1 is a perspective view of a first embodiment of a microfluidic delivery device 10 which may be used in the present invention. Delivery device 10 includes a film 20 having first outwardly facing major surface 22 and second outwardly facing major surface 24. First outwardly facing major surface 22 has a plurality of outlet ports 32 disposed thereon. In addition, a sensor 12 operatively connected to the delivery device 10 which can be coupled, e.g., to detect the amount of a liquid delivered over time.

In FIG. 1, delivery device 10 is shown to have a rectangular footprint. Film 20 of delivery device 10 may also have a variety of shapes, depending on the location of skin treatment. Possible shapes of the footprint left by film 20 include, but are not limited to, squares, rectangles, triangles, circles, ovals, kidneys, stars, crosses, characters, etc. The corners of such shapes, if any, may be angular or curved to reduce potential lift/removal points. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

Delivery device 10 of FIG. 1 is shown to be planar. In some embodiments, the array may be curvilinear. The curvilinear delivery devices shaped to the body surface may provide superior retention of the array to the isolated body part under treatment.

Outlet ports 32 disposed on film 20 are shown to have circular cross-sections in FIG. 1, but may also have a variety of cross-sectional shapes. Possible shapes for outlet ports 32 include, but are not limited to, square, rectangular, triangular, circular, oval, kidney-shapes, stars, crosses, characters, etc.

Film 20 element of delivery device 10 preferably is relatively thin and flexible, so that it preferably readily conforms to the user's skin and is comfortable to wear, both because of the flexibility and conformability, as well as from the thinness. Delivery device 10 of the present invention may be intended for extended wear preferably are also formed to be aesthetically elegant without either peeling, wrinkling, cracking, or appearing greasy or tacky, or otherwise unpleasant or unsightly in nature. Delivery device 10 preferably is formed with sufficient rigidity and integrity to be able to withstand normal use when on the skin. In some embodiments, delivery device 10 of the invention preferably is formed with sufficient strength to stay intact on the skin when exposed to normal external forces that the skin may experience, such as rubbing of clothing.

In some embodiments, first outwardly facing major surface 22 of film 20 has disposed thereon an adhesive layer. The adhesive layer may be used to give delivery device 10 the sufficient strength to stay intact on the skin when exposed to normal external forces. Other means of creating sufficient strength to delivery device 10 so that the array stays intact on the skin will be discussed below.

FIG. 2 is a cross-sectional view of a section of delivery device 10 along the 2-2 plane of FIG. 1. The figure shows a liquid reservoir 30 contained within film 20, as well as a plurality of outlet ports 32 disposed on first outwardly facing major surface 22 of film 20. Benefit agent is disposed in liquid reservoir 30. Microfluidic channels 34 (having a transverse dimension between about 100 nanometers and about 0.5 millimeter) are disposed within film 20 and in fluid communication with reservoir 30. Outlet ports 32 are operatively connected to first outwardly facing major surface 22 of film 20 in fluid communication with at least one microfluidic channel 34.

The figure also shows microfluidic channels 34 as being of constant width from liquid reservoir 30 to outlet ports 32. In other embodiments, microfluidic channels 34 may be tapered from one end to the other. If they are tapered from wider at liquid reservoir 30 to thinner at outlet ports 32, capillary flow may aid in the movement of the liquid to outwardly facing major surface 22 of film 20.

Benefit agent is disposed in liquid reservoir 30. In some embodiments, the benefit agent is disposed in liquid reservoir 30 during the manufacturing process. In other embodiments, the benefit agent is disposed in liquid reservoir 30 after microfluidic delivery device 10 has been made (post manufacturing).

In some embodiments, benefit agent is disposed in liquid reservoir 30 post manufacturing by filling liquid reservoir 30 via one or more of microfluidic channels 34. In other embodiments, microfluidic delivery device 10 can be manufactured with fill channels (not shown) operatively connected to first outwardly facing major surface 22 or second outwardly facing major surface 24 of film 20 which are in fluid communication with liquid reservoir 30.

In the embodiment shown in FIG. 2, there is one liquid reservoir 30 contained within film 20. Liquid reservoir 30 is disposed closer to second outwardly facing major surface 24 than to first outwardly facing major surface 22. In other embodiments, there may be multiple liquid reservoirs, and they may be in different locations within the film comprising the delivery device. FIG. 3 is a cross-sectional view of a second embodiment of a microfluidic delivery device 100 along a similar 2-2 plane. Delivery device 100 includes a film 120 having first outwardly facing major surface 122 and second outwardly facing major surface 124. First outwardly facing major surface 122 has a plurality of first outlet ports 132 and second outlet ports 142 disposed thereon.

First liquid reservoir 130 and second liquid reservoir 140 are contained within film 120. The same, or different, benefit agents may be disposed in liquid reservoirs 130 and 140. First microfluidic channels 134 disposed within film 120 are in fluid communication with first liquid reservoir 130, with outlet ports 132 operatively connected to first outwardly facing major surface 122 of film 120 in fluid communication with at least one first microfluidic channel 134. Second microfluidic channels 144 disposed within film 120 are in fluid communication with second liquid reservoir 140, with second outlet ports 142 operatively connected to first outwardly facing major surface 122 of film 120 in fluid communication with at least one second microfluidic channel 144. In this embodiment, first liquid reservoir 130 is disposed closer to second outwardly facing major surface 124 than second liquid reservoir 140.

The pattern of microfluidic channels is the integrated network of microfluidic channels, which, in some embodiments, can intersect at predetermined points. In FIGS. 2 and 3, the pattern is simple. The microfluidic channels flow in straight line paths form the liquid reservoirs to the first outwardly facing major surface of the film. In other embodiments, the pattern of microfluidic channels, or the pattern of the liquid reservoirs, may be more complex.

FIG. 4 is a cross-sectional view of a third embodiment of a microfluidic delivery device 200 along a similar 2-2 plane. Delivery device 200 includes a film 220 having first outwardly facing major surface 222 and second outwardly facing major surface 224. First outwardly facing major surface 222 has a plurality of outlet ports disposed thereon. In this embodiment, there are four liquid reservoirs contained within film 220: first liquid reservoir 230, second liquid reservoir 240, third liquid reservoir 250, and fourth liquid reservoir 260. The same, or different benefit agents may be disposed in liquid reservoirs 230, 240, 250, and 260.

First microfluidic channels 234a and 234b disposed within film 220 are in fluid communication with first liquid reservoir 230, with outlet ports 232a operatively connected to first outwardly facing major surface 222 of film 220 in fluid communication with at least one first microfluidic channel 234a, and outlet ports 232b operatively connected to first outwardly facing major surface 222 of film 220 in fluid communication with at least one first microfluidic channel 234b. Outlet ports 232b are significantly further from first liquid reservoir 230 than are outlet ports 232a.

Second microfluidic channel 244 disposed within film 220 is in fluid communication with second liquid reservoir 240, with second outlet port 245 operatively connected to first outwardly facing major surface 222 of film 220 in fluid communication with second microfluidic channel 244. Third microfluidic channels 254a and 254b disposed within film 220 are in fluid communication with third liquid reservoir 250. Second outlet port 245 is also operatively connected to first outwardly facing major surface 222 of film 220 in fluid communication with third microfluidic channel 254a. Third microfluidic channel 254a is in fluid communication with third liquid reservoir 250. So, in this embodiment, second microfluidic channel 244 and third microfluidic channel 254a intersect at second outlet port 245, thereby allowing the contents of second liquid reservoir 240 to mix with the contents of third liquid reservoir 250.

Third outlet port 255 is operatively connected to first outwardly facing major surface 222 of film 220 in fluid communication with third microfluidic channel 254b and with third liquid reservoir 250. Third outlet port 255 is also operatively connected to first outwardly facing major surface 222 of film 220 in fluid communication with fourth microfluidic channel 264a. Fourth microfluidic channel 264a disposed within film 220 is also in fluid communication with fourth liquid reservoir 260. So, in this embodiment, third microfluidic channel 254a and fourth microfluidic channel 264a intersect at third outlet port 255, thereby allowing the contents of third liquid reservoir 250 to mix with the contents of fourth liquid reservoir 260.

Finally, fourth outlet port 262 is operatively connected to first outwardly facing major surface 222 of film 220 in fluid communication with fourth microfluidic channel 264b. Fourth microfluidic channel 264b disposed within film 220 is in fluid communication with fourth liquid reservoir 260. So, the contents of fourth liquid reservoir 260 may be delivered to the surface of the skin without being mixed with the contents of any other liquid reservoir.

Figure 5:
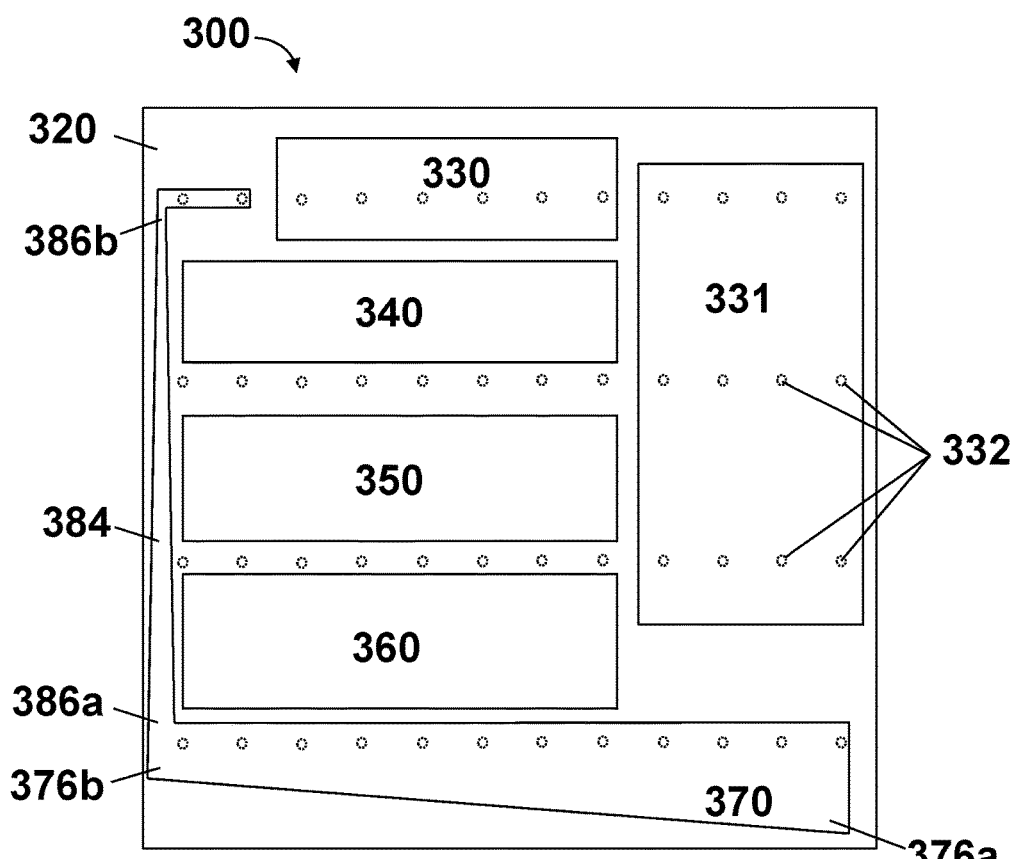
FIG. 5 is a cross-sectional view of a fourth embodiment of the microfluidic delivery device of FIG. 1 along the 5-5 plane.

The pattern of microfluidic channels in the third embodiment (shown in FIG. 4) is more complex than that shown in the first two embodiments. A more complex pattern of both of microfluidic channels and liquid reservoirs is shown in FIG. 5. The figure is a cross-sectional view of a fourth embodiment of the microfluidic delivery device of the present invention shown along the 5-5 plane of the device of FIG. 1. In this embodiment, delivery device 300 includes a film 320 having first and second outwardly facing major surfaces (not shown). There are six liquid reservoirs in delivery device 300: first liquid reservoir 330, second liquid reservoir 331, third liquid reservoir 340, fourth liquid reservoir 350, fifth liquid reservoir 360, and sixth liquid reservoir 370. Shown in dotted lines are outlet ports 332 which are located on first outwardly facing major surface.

All outlet ports 332 are operatively connected to first outwardly facing major surface of film 320 in fluid communication with microfluidic channels as well as liquid reservoirs in the film. Outlet ports 332 located directly above first liquid reservoir 330 and second liquid reservoir 331 yield a pattern with the flow in the microfluidic channels (not shown) being in straight line paths from liquid reservoirs 330 and 331 to the first outwardly facing major surface of the film. Outlet ports 332 located between third liquid reservoir 340 and fourth liquid reservoir 350, or between fourth liquid reservoir 350 and fifth liquid reservoir 360 may be fed by one, or more than one, microchannel (not shown).

Liquid reservoirs 330, 331, 340, 350, and 360 disposed in film 320 are shown to have rectangular cross-sections in FIG. 5, but may also have a variety of cross-sectional shapes. Possible shapes for the liquid reservoirs include, but are not limited to, square, rectangular, triangular, circular, oval, kidney-shapes, stars, crosses, etc.

Sixth liquid reservoir 370 is shown to taper from first end 376a to second end 376b. Outlet ports 332 located directly above sixth liquid reservoir 370 yield a pattern with the flow in the microfluidic channels (not shown) being in straight line paths from sixth liquid reservoir 370 to the first outwardly facing major surface of the film. Microchannel 384 is shown as permitting the flow of liquid from second end 376b of sixth liquid reservoir 370 to the far side of delivery device 300. Microchannel 384 is tapered from first end 386a to second end 386b. This may be done to enhance the capillary flow of liquid from first to second end of microchannel 384.

All the embodiments discussed thus far are used to deliver benefit agent(s) to patients at surface of the skin. To address the challenge of intact skin, a variety of microneedle-array based microfluidic delivery devices may be used.

Figure 6:
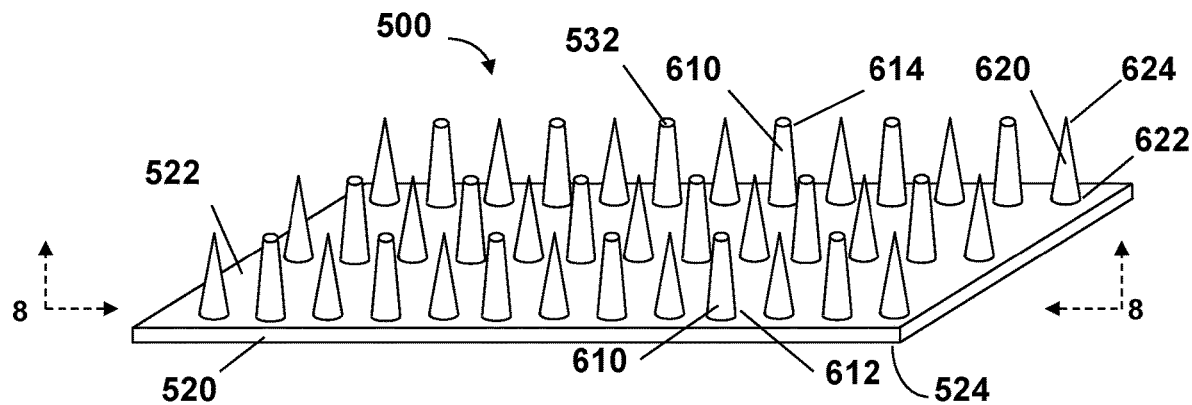
FIG. 6 is a perspective view of a fifth embodiment microfluidic delivery device of the present invention.

FIG. 6 is a perspective view of a fifth embodiment microfluidic delivery device 500 which may be used in the present invention. Delivery device 500 includes a film 520 having first outwardly facing major surface 522 and second outwardly facing major surface 524. First outwardly facing major surface 522 has a plurality of stratum corneum piercing hollow bore microneedles 610 and stratum corneum piercing solid microneedles 620 extending therefrom. Each hollow bore microneedle 610 has a proximal end 612 and a distal end 614, where proximal end 612 is the end of hollow bore microneedle 610 disposed on first outwardly facing major surface 522 of a delivery device 500. Outlet ports 532 are disposed on distal end 614 of hollow bore microneedle 610. Each solid microneedle 620 has a proximal end 622 and a distal end 624, where proximal end 622 is the end of hollow bore microneedle 620 disposed on first outwardly facing major surface 522 of a delivery device 500.

Delivery device 500 is shown to have a rectangular footprint. Film 520 of delivery device 500 may also have a variety of shapes including, but are not limited to, squares, rectangles, triangles, circles, ovals, kidneys, stars, crosses, characters, etc. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

Delivery device 500 of FIG. 6 is shown to be planar. In some embodiments, the array may be curvilinear. The curvilinear delivery devices shaped to the body surface provides microneedles 610, 620 oriented normal to that surface. This provides better penetration of the microneedles and retention of the array for treatment.

Film 520 element of delivery device 500 preferably is relatively thin and flexible, so that it readily conforms to the user's skin and is comfortable to wear because of its conformability. Device 500 may be intended for extended wear, so is formed to be aesthetically elegant without either peeling, wrinkling, cracking, or appearing greasy or tacky, or otherwise unpleasant or unsightly in nature. The device preferably is formed with sufficient rigidity and integrity to be able to withstand normal use when on the skin of the user.

In some embodiments, delivery device 500 is formed with sufficient strength to stay intact on the skin when exposed to normal external forces that the skin may experience, such as rubbing of clothing. In some embodiments, hollow bore microneedles 610 and stratum corneum piercing solid microneedles 620 are sufficient to keep delivery device 500 intact on the skin. In other embodiments, first outwardly facing major surface 522 of film 520 has disposed thereon an adhesive layer. The adhesive layer may be used to give delivery device 500 the sufficient strength to stay intact on the skin when exposed to normal external forces. Alternatively, microneedles 610, 620 may have a desired surface structure, such as slight directional ridges, to hold needle in place.

Figure 7:
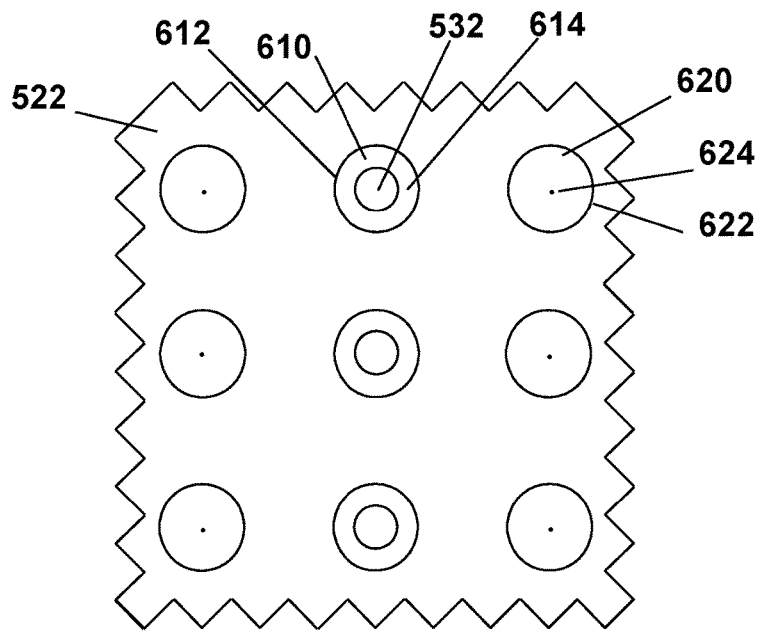
FIG. 7 is a top view of a section of the microfluidic delivery device of FIG. 6.

FIG. 7 is a top view of a section of the delivery device of FIG. 6. The figure shows stratum corneum piercing hollow bore microneedles 610 and stratum corneum piercing solid microneedles 620 extending from facing major surface 522 of a delivery device 500. Each hollow bore microneedle 610 has a proximal end 612 and a distal end 614. Each solid microneedle 620 has a proximal end 622 and a distal end 624.

Outlet ports 532 disposed on distal end 614 of hollow bore microneedle 610 are shown to have circular cross-sections in FIG. 7, but may also have a variety of cross-sectional shapes. Possible shapes for outlet ports 532 include, but are not limited to, square, rectangular, triangular, circular, oval, kidney-shapes, stars, crosses, etc.

As shown in the figure, hollow bore microneedles 610 and solid microneedles 620 are arranged in rows in a uniform a square pattern on first outwardly facing major surface 522 of delivery device 500. In other embodiments, 610 and solid microneedles 620 may be arranged in other patterns.

Figure 8:
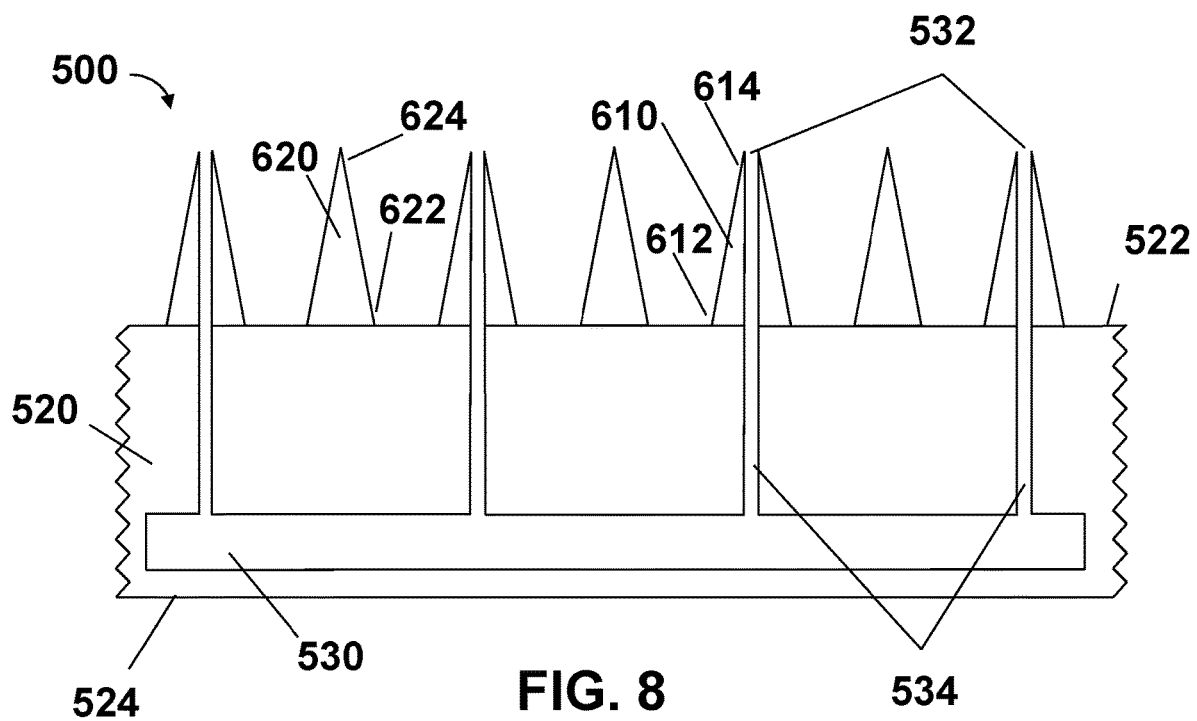
FIG. 8 is a cross-sectional view of a section of the microfluidic delivery device of FIG. 6 along the 8-8 plane.

FIG. 8 is a cross-sectional view of a section of delivery device 500 along the 8-8 plane of FIG. 6. The figure shows a liquid reservoir 530 contained within film 520. In addition, the figure shows a plurality solid microneedle 620, each solid microneedle having a proximal end 622 and a distal end 624, as well as a plurality of hollow bore microneedles 610, each hollow bore solid microneedle having a proximal end 622 and a distal end 624. Each hollow bore microneedle 610 has an outlet port 532 disposed on its distal end 614.

Benefit agent is disposed in liquid reservoir 530. Microfluidic channels 534 (having a transverse dimension between about 100 nanometers and about 0.5 millimeter) are disposed within film 520 and in fluid communication with reservoir 530. Outlet ports 532 are operatively connected to distal ends 614 of hollow bore microneedles 610 in fluid communication with at least one microfluidic channel 534.

The figure shows microfluidic channels 534 as being of constant width from liquid reservoir 530 to outlet ports 532. In other embodiments, microfluidic channels 534 may be tapered from one end to the other. If they are tapered from wider at liquid reservoir 530 to thinner at outlet ports 532, capillary flow may aid in the movement of the liquid from liquid reservoir 530 to outlet ports 532.

Solid microneedles 620 may be surface-coated with a benefit agent, or may be made of biodegradable, bioabsorbable, or dissolvable materials in which one, or several, benefit agents have been mixed.

The dimensions of microneedles 610, 620 may vary depending on a variety of factors such as the type of benefit agent to be delivered, the dosage of the benefit agent to be delivered, and the desired penetration depth. Generally, the stratum corneum piercing microneedles are constructed to provide skin-piercing and benefit agent delivery functions and thus will be designed to be sufficiently robust to withstand insertion into and withdrawal from the skin. Each microneedle has a length of about 1 micrometer (μm) to about 5000 micrometers (μm), or about 1 μm to about 500 μm, or about 100 μm to about 500 μm. The penetration length of the microneedles into the biological barrier is about 50 μm to about 200 μm. In addition, each of the microneedles has a width of about 1 μm to about 500 μm. Furthermore, each microneedle has a thickness of about 1 μm to about 200 μm. It will be understood by one skilled in the art that the width and thickness of the stratum corneum piercing microneedle may vary along its length. For instance, the base portion may be wider (thicker) than the body portion, or the body portion may have a slight taper approaching the tip portion.

Generally, stratum corneum piercing microneedles 610, 620 can be in any elongated shape suitable for providing the skin piercing and benefit agent delivery, with minimal pain to the patient. In various embodiments, an individual microneedle is substantially cylindrical, wedge-shaped, cone-shaped, or triangular (e.g., blade-like). The cross-sectional shape (cut along a plane approximately parallel to the planar substrate or approximately perpendicular to the longitudinal axis of the microneedle) of the microneedle, or at least the portion of the microneedle that is penetrable into the skin, may take a variety of forms, including rectangular, square, oval, circular, diamond, triangular, or star-shaped.

The tip portions of stratum corneum piercing microneedles 610, 620 are designed to pierce a biological barrier, e.g., to pierce the stratum corneum of the skin of a patient, to deliver benefit agents into the patient's tissue. Preferably, the tip portion of each microneedle should be sufficiently small and sharp to enable piercing and penetration of the skin with minimal pain. In a preferred embodiment, the tip end portion of the microneedle is tapered from the body portion toward the tip end, defining a point or apex at the end of the microneedle. In various embodiments, the tapered tip portion may be in the form of an oblique angle at the tip, or a pyramidal or conical or triangular shape.

Figure 9:
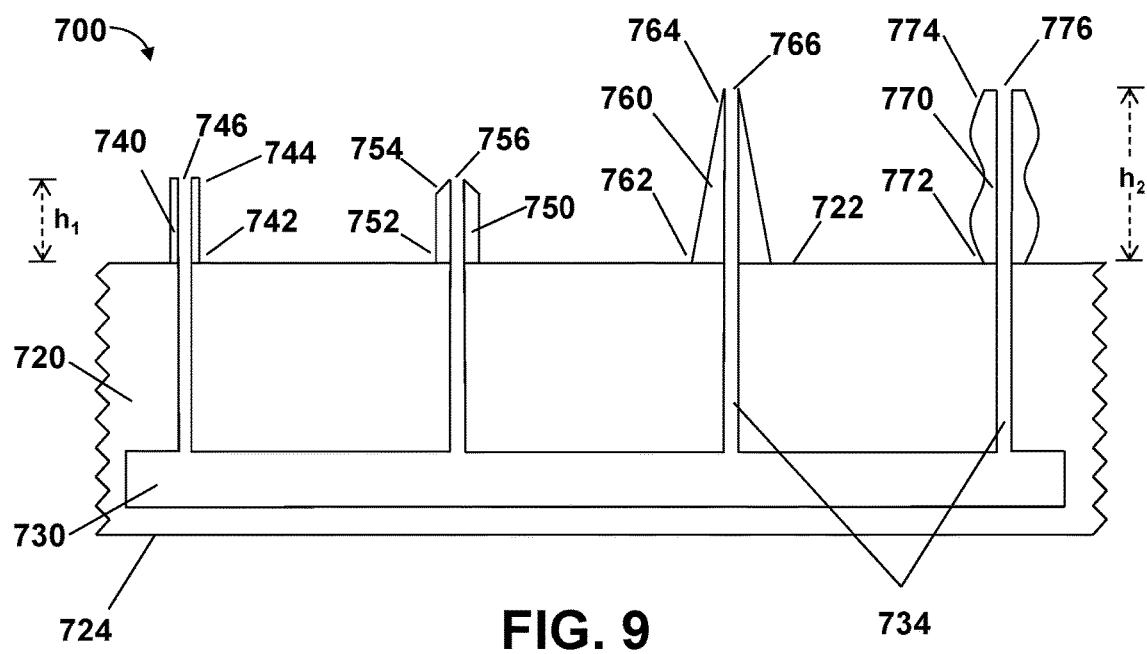
FIG. 9 is a cross-sectional view of a section of a sixth embodiment microfluidic delivery device.

Microneedles in delivery devices of the invention may also be of a variety of lengths and geometries. FIG. 9 is a cross-sectional view of a section of a sixth embodiment delivery device 700. Delivery device 700 includes a film 720 having first outwardly facing major surface 722 and second outwardly facing major surface 724. The figure shows a liquid reservoir 730 contained within film 720. First outwardly facing major surface 722 has a plurality of stratum corneum piercing hollow bore microneedles 740, 750, 760, and 770 extending therefrom.

In this embodiment, a variety of hollow bore microneedle stratum corneum piercing microneedle lengths and shapes are presented. Hollow bore microneedle 740 is cylindrical in shape, with no taper from proximal end 742 to distal end 744. Outlet port 746 is disposed on distal end 744 of hollow bore microneedle 740. Hollow bore microneedle 750 has a cylindrical proximal end 752, which tapers to a point at distal end 754. Outlet port 756 is disposed on distal end 754 of hollow bore microneedle 750. Hollow bore microneedle 760 is conical in shape, with a taper from proximal end 762 to distal end 764. Outlet port 766 is disposed on distal end 764 of hollow bore microneedle 760. Finally, hollow bore microneedle 770 has a proximal end 772 and a distal end 774, and has an undulating shape. Outlet port 776 is disposed on distal end 774 of hollow bore microneedle 770.

Hollow bore microneedles 740 and 750 extend from first outwardly facing major surface 722 of film 720 to a height of $h_1$, while hollow bore microneedles 760 and 770 extend from first surface 722 of film 720 to a height of $h_2$.

Benefit agent is disposed in liquid reservoir 730. Microfluidic channels 734 (transverse dimension between about 100 nanometers and about 0.5 millimeter) are disposed within film 720 and in fluid communication with reservoir 730. Outlet ports 746, 756, 766, and 776 are in fluid communication with at least microfluidic channels 734.

In this embodiment, height $h_2$ is greater than height of $h_1$, and there may be a desire for both a shallower and a deeper penetration into the skin of the user for the benefit agent contained in liquid reservoir 730. Although the figure shows hollow bore microneedles 740 and 750 are of uniform height $h_1$, while hollow bore microneedles 760 and 770 are of uniform height $h_2$, it is to be understood that in other embodiments the microneedles may be of any number of different heights.

Figure 10:
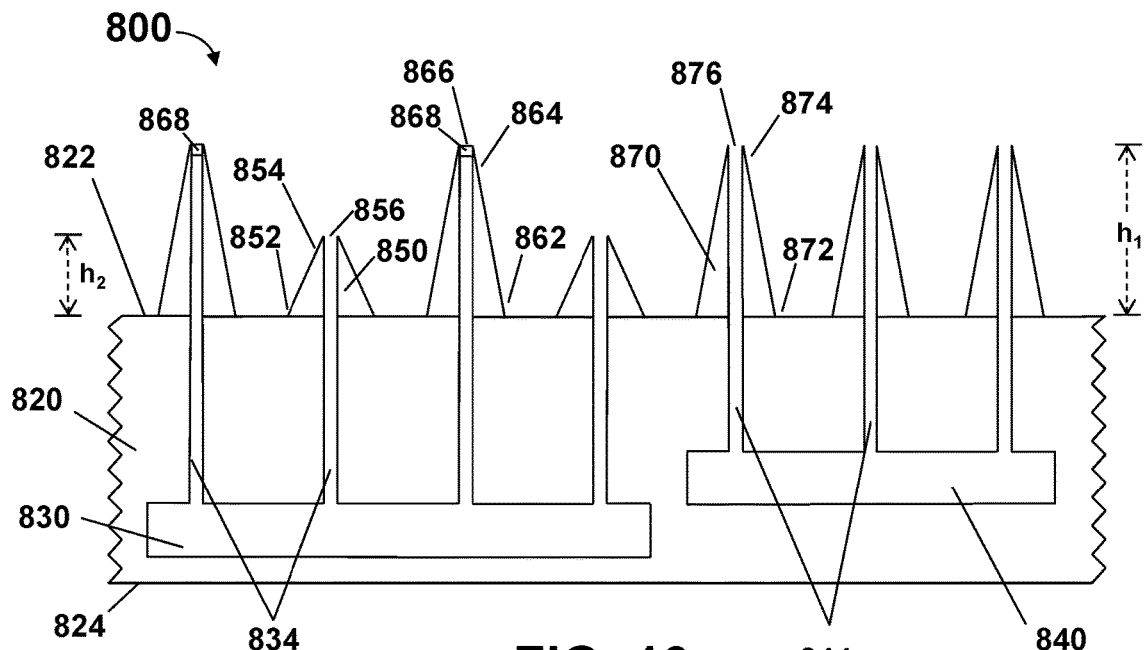
FIG. 10 is a cross-sectional view of a section of a seventh embodiment microfluidic delivery device.
Figure 11:
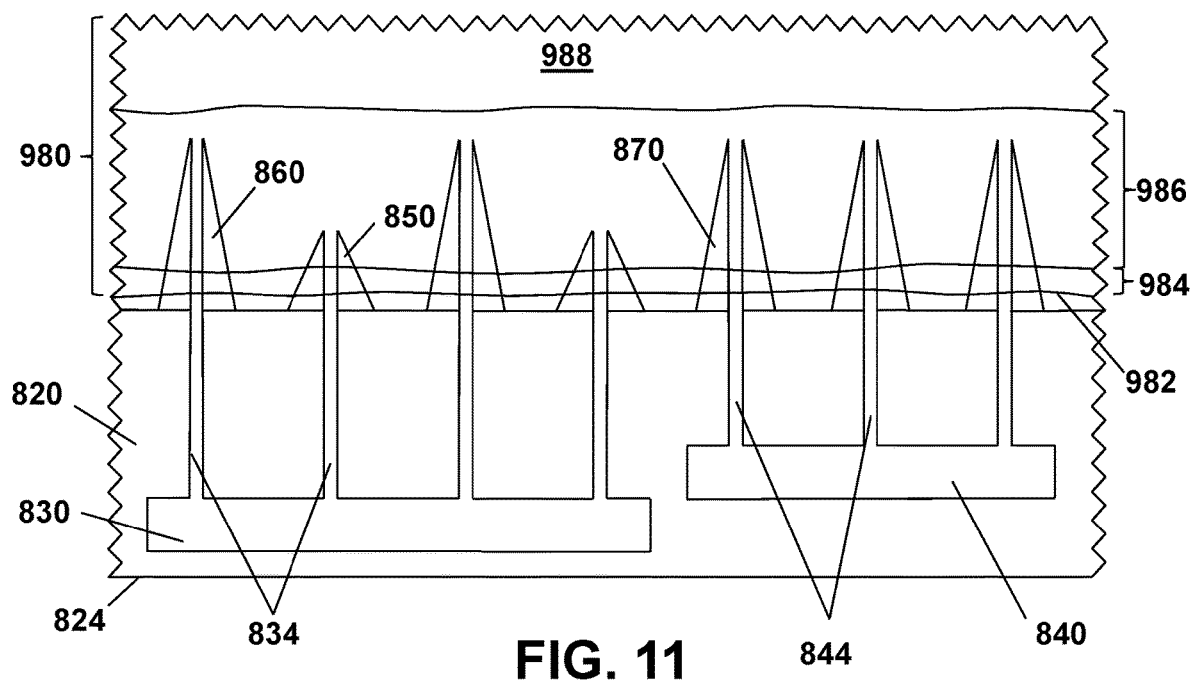
FIG. 11 is a cross-sectional view of a section of the microfluidic delivery device of FIG. 10 after the microneedles have penetrated the patient's skin.

FIG. 10 is a cross-sectional view of a seventh embodiment of a microfluidic delivery device 800. Delivery device 800 includes a film 820 having first outwardly facing major surface 822 and second outwardly facing major surface 824. The figure shows first liquid reservoir 830 and second liquid reservoir 840 contained within film 820. Hollow bore microneedles 850, 860, and 870 extend from first outwardly facing major surface 822 of film 820.

Hollow bore microneedles 850 are conical in shape, tapering from proximal end 852 to distal end 854. Microneedles 850 extend from first outwardly facing major surface 822 of film 820 to a height of $h_1$. Outlet port 856 is disposed on distal end 854 of hollow bore microneedle 850.

Hollow bore microneedles 860 are conical in shape, tapering from proximal end 862 to distal end 864. Microneedles 860 extend from first outwardly facing major surface 822 of film 820 to a height of $h_2$. Outlet port 866 is disposed on distal end 864 of hollow bore microneedle 860.

Hollow bore microneedles 870 are conical in shape, tapering from proximal end 872 to distal end 874. Microneedles 870 extend from first outwardly facing major surface 822 of film 820 to a height of $h_2$. Outlet port 876 is disposed on distal end 874 of hollow bore microneedle 870.

Although FIG. 10 shows hollow bore microneedles 850, 860, and 870 of different heights ($h_1$, $h_2$, and $h_3$, respectively), it is to be understood that in other embodiments the microneedles may all be of the same height, or any number of different heights.

First liquid reservoir 830 and second liquid reservoir 840 are contained within film 820. The same, or different, benefit agents may be disposed in liquid reservoirs 830 and 840. First microfluidic channels 834 disposed within film 820 are in fluid communication with first liquid reservoir 830, with outlet ports 856 and 866 operatively connected to first outwardly facing major surface 822 of film 820 in fluid communication with at least one first microfluidic channel 834. Second microfluidic channels 844 disposed within film 820 are in fluid communication with second liquid reservoir 840, with second outlet ports 876 operatively connected to first outwardly facing major surface 822 of film 820 in fluid communication with at least one second microfluidic channel 844. In this embodiment, first liquid reservoir 830 is disposed closer to second outwardly facing major surface 124 than second liquid reservoir 840.

Obstructors 868 are disposed in first microfluidic channels 834 near distal end 864 of hollow bore microneedle 860. In some embodiments, obstructors 868 act as valves which may open and close to permit the flow of benefit agents from first liquid reservoir 830. In other embodiments, obstructors 868 may be made of biodegradable, bioabsorbable, or dissolvable materials. In these embodiments, release of benefit agents from first liquid reservoir 830 may be initiated when biodegradable obstructors 868 break down when subjected to bodily fluids.

Seventh embodiment microfluidic delivery device 800 is demonstrated in a prophetic use in FIG. 10. The figure is a cross-sectional view of a section of the microfluidic delivery device 800 after the microneedles have penetrated the patient's skin. The figure shows skin tissue 980 with an outer surface 982. Beneath outer surface 982 lies the epidermis 984, dermis 986, and the subcutis or hypodermis 988 layers. The first outwardly facing major surface 822 of film 820 is in contact with outer surface 982 of skin tissue 980.

Hollow bore microneedle 850, 860, and 870 all penetrate outer surface 982 and epidermis 944. Microneedles 860 and 870 penetrate deeper into dermis 986 than microneedles 850. So, if there is a desire for personalized treatment at different skin depths, delivery devices 800 of the present invention allow a degree of flexibility not available to delivery devices produced using the microcasting process.

Figure 12:
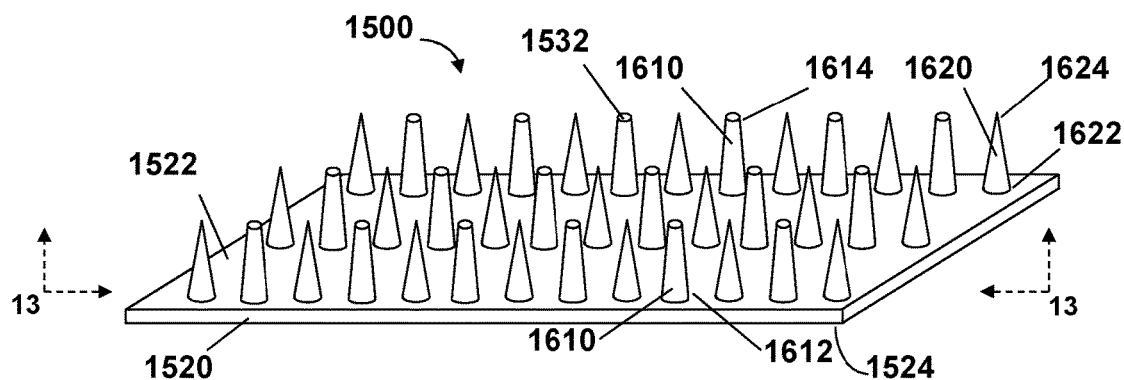
FIG. 12 is a perspective view of an eighth embodiment microfluidic delivery device of the present invention.

The microfluidic delivery devices presented thus far in the present invention are single use devices with single-use liquid reservoirs. In some embodiments, the reservoirs may be refillable. FIG. 12 is a perspective view of an eighth embodiment of a microfluidic delivery device 1500 which may be used in the present invention. Delivery device 1500 includes a film 1520 having first outwardly facing major surface 1522 and second outwardly facing major surface 1524. First outwardly facing major surface 1522 has a plurality of stratum corneum piercing hollow bore microneedles 1610 and stratum corneum piercing solid microneedles 1620 extending therefrom. Each hollow bore microneedle 1610 has a proximal end 1612 and a distal end 1614, where proximal end 1612 is the end of hollow bore microneedle 1610 disposed on first outwardly facing major surface 1522 of a delivery device 1500. Outlet ports 1532 are disposed on distal end 1614 of hollow bore microneedle 1610. Each solid microneedle 1620 has a proximal end 1622 and a distal end 1624, where proximal end 1622 is the end of hollow bore microneedle 1620 disposed on first outwardly facing major surface 1522 of a delivery device 1500.

Delivery device 1500 is shown to have a rectangular footprint, but may also have a variety of shapes, such as squares, rectangles, triangles, circles, ovals, kidneys, stars, crosses, characters, etc. The zone of the treatment could be greater than about 1,000 $cm^2$, about 1,000 $cm^2$, or about 100 $cm^2$, or about 10 $cm^2$, or about 1 $cm^2$, or less than 1 $cm^2$.

Delivery device 1500 of FIG. 12 is shown to be planar. In some embodiments, the array may be curvilinear. The curvilinear delivery devices shaped to the body surface provides microneedles 1610, 1620 oriented normal to that surface. This provides better penetration of the microneedles and retention of the array for treatment.

Film 1520 element of delivery device 1500 preferably is relatively thin and flexible, so that it readily conforms to the user's skin and is comfortable to wear because of its conformability is formed with sufficient strength to stay intact on the skin when exposed to normal external forces that the skin may experience, such as rubbing of clothing. Hollow bore microneedles 1610 and stratum corneum piercing solid microneedles 1620 may be sufficient to keep delivery device 1500 intact on the skin. However, first outwardly facing major surface 1522 of film 1520 may have an adhesive layer disposed thereon. The adhesive layer may be used to give delivery device 1500 the sufficient strength in some embodiments to stay intact on the skin when exposed to normal external forces. Alternatively, microneedles 1610, 1620 may have a desired surface structure, such as slight directional ridges, to hold needle in place.

Outlet ports 1532 disposed on distal end 1614 of hollow bore microneedle 1610 are may have a variety of cross-sectional shapes. Possible shapes for outlet ports 1532 include, but are not limited to, square, rectangular, triangular, circular, oval, kidney-shapes, crosses, etc.

As shown in the figure, hollow bore microneedles 1610 and solid microneedles 1620 are arranged in rows in a uniform a square pattern on first outwardly facing major surface 1522 of delivery device 1500. In other embodiments, 1610 and solid microneedles 1620 may be arranged in other patterns.

Figure 13:
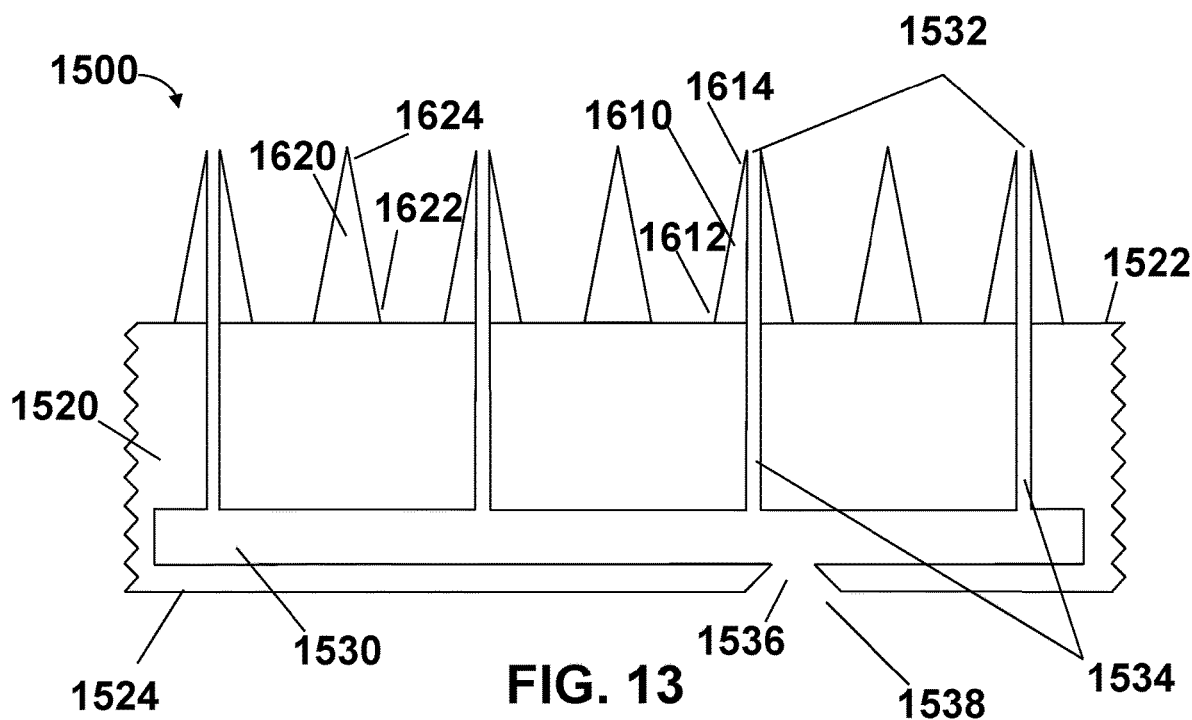
FIG. 13 cross-sectional view of a section of the microfluidic delivery device of FIG. 12 along the 12-12 plane.

FIG. 13 is a cross-sectional view of a section of delivery device 1500 along the 12-12 plane of FIG. 12. The figure shows a liquid reservoir 1530 contained within film 1520. In addition, the figure shows a plurality solid microneedle 1620, each solid microneedle having a proximal end 1622 and a distal end 1624, as well as a plurality of hollow bore microneedles 1610, each hollow bore solid microneedle having a proximal end 1622 and a distal end 1624. Each hollow bore microneedle 1610 has an outlet port 1532 disposed on its distal end 1614.

Benefit agent is disposed in liquid reservoir 1530. Microfluidic channels 1534 (having a transverse dimension between about 100 nanometers and about 0.5 millimeter) are disposed within film 1520 and in fluid communication with reservoir 1530. Outlet ports 1532 are operatively connected to distal ends 1614 of hollow bore microneedles 1610 in fluid communication with at least one microfluidic channel 1534.

The figure shows microfluidic channels 1534 as being of constant width from liquid reservoir 1530 to outlet ports 1532. In other embodiments, microfluidic channels 1534 may be tapered from one end to the other. If they are tapered from wider at liquid reservoir 1530 to thinner at outlet ports 1532, capillary flow may aid in the movement of the liquid from liquid reservoir 1530 to outlet ports 1532.

As mentioned earlier, in this embodiment microfluidic delivery device 1500 has a fillable or refillable liquid reservoir 1530. FIG. 13 shows inlet port 1538 disposed on second outwardly facing major surface 1524 of film 1520. Refill channel 1536 is disposed within film 1520 and in fluid communication with reservoir 1530. Inlet port 1538 is in fluid communication with refill channel 1536.

Refill channel 1536 may be microfluidic in nature, i.e. having a transverse dimension between about 100 nanometers and about 0.5 millimeter. The figure shows refill channel 1536 being tapered from wider at second outwardly facing major surface 1524 to narrower at refillable liquid reservoir 1530. In some embodiments, refill channel 1536 may be of constant width from liquid reservoir 1530 to inlet port 1538. In still other embodiments, refill channel 1536 may be tapered from wider at refillable liquid reservoir 1530 to narrower at second outwardly facing major surface 1524.

Inlet port 1538 may have a variety of cross-sectional shapes. Possible shapes for inlet port 1538 include, but are not limited to, square, rectangular, triangular, circular, oval, kidney-shapes, crosses, etc. In some embodiments, inlet port 1538 may be shaped so as to adapt to the device used to refill liquid reservoir 1530.

Solid microneedles 1620 may be surface-coated with a benefit agent, or may be made of biodegradable, bioabsorbable, or dissolvable materials in which one, or several, benefit agents have been mixed.

Similar to the dimensions of microneedles 610, 620 discussed previously, microneedles 1610, 1620 may have lengths of about 1 micrometer (μm) to about 5000 micrometers (μm), widths of about 1 μm to about 500 μm, and thicknesses of about 1 μm to about 200 μm. It will be understood by one skilled in the art that the width and thickness of the stratum corneum piercing microneedle may vary along its length. For instance, the base portion may be wider (thicker) than the body portion, or the body portion may have a slight taper approaching the tip portion.

Stratum corneum piercing microneedles 1610, 1620 can be in any elongated shape suitable for providing the skin piercing and benefit agent delivery, with minimal pain to the patient, with individual microneedles being substantially cylindrical, wedge-shaped, cone-shaped, or triangular (e.g., blade-like). The cross-sectional shape (cut along a plane approximately parallel to the planar substrate or approximately perpendicular to the longitudinal axis of the microneedle) of the microneedle, or at least the portion of the microneedle that is penetrable into the skin, may take a variety of forms, including rectangular, square, oval, circular, diamond, triangular, or star-shaped.

The tip portions of stratum corneum piercing microneedles 1610, 1620 are designed to pierce a biological barrier, e.g., to pierce the stratum corneum of the skin of a patient, to deliver benefit agents into the patient's tissue. Preferably, the tip portion of each microneedle should be sufficiently small and sharp to enable piercing and penetration of the skin with minimal pain. In a preferred embodiment, the tip end portion of the microneedle is tapered from the body portion toward the tip end, defining a point or apex at the end of the microneedle. In various embodiments, the tapered tip portion may be in the form of an oblique angle at the tip, or a pyramidal or conical or triangular shape.

In a preferred embodiment, at least two independent liquid systems each includes a fillable reservoir 1530 having an inlet port 1538 and coupled to at least one microfluidic channel 1534 associated with at least one microneedle 1610.

In some embodiments, film 20, 120, 220, 320, are formed of, or coated with, a biocompatible material. In some embodiments, film 520, 720, 820, 1520, stratum corneum piercing microneedles 620, 740, 750, 760, 770, 850, 860, 870, 1610, 1620, or both, are formed of, or coated with, a biocompatible material. Microneedles 620, 740, 750, 760, 770, 850, 860, 870, 1610, 1620, may be formed from the same material used in film 520, 720, 820, 1520, or alternatively, the microneedles can include a material different from the film material. Representative examples of suitable materials of construction include metals and alloys such as stainless steels, palladium, titanium, and aluminum; plastics such as polyetherimide, polycarbonate, polyetheretherketone, polyimide, polymethylpentene, polyvinylidene fluoride, polyphenylsulfone, liquid crystalline polymer, polyethylene terephthalate (PET), polyethylene terephthalate-glycol modified (PETG), and polyimide; and ceramics such as silicon and glass. The material preferably is selected such that the microneedle is strong enough at its designed dimensions for the microneedle to effectively pierce the skin without significant bending or breaking of the microneedle. The microneedle and substrate materials also should be non-reactive with the drug formulation being delivered by the delivery device.

In some embodiments, the films, microneedles, or both, are formed of biodegradable or bioabsorbable materials. Representative examples of suitable materials include, but are not limited to, poly(lactic acid) (PLA), poly(glycolic acid) (PGA), polydioxanone (PDO), poly(epsilon-caprolactone) (PCL), poly(lactic-co-glycolic acid) (PLGA), poly (ortho ester) (POE), copoly(ether-ester) (CEE), based formulations, or combinations of such materials. Microneedles can be formed from water soluble materials that include polyvinyl alcohol (PVOH), carboxymethylcellulose (CMC) and polyethylene oxide (PEO) based formulations, or combinations of such materials.

Films, stratum corneum piercing microneedles, or both, optionally may further include secondary materials of construction embedded therein or coated thereon. For example, microparticles, nanoparticles, fibers, fibrids, or other particulate materials may be included. These secondary materials may enhance one or more physical or chemical characteristics of delivery device 10, 100, 200, 300, 500, 700, 800, 1500.

In some embodiments, stratum corneum piercing microneedles 620, 740, 750, 760, 770, 850, 860, 870, 1610, 1620, are formed of biodegradable materials, while film 520, 720, 820, 1520, is not biodegradable. In these embodiments the benefit agent material can comprise dissoluble materials or insoluble but dispersible materials. So, the mechanism of delivery of the benefit agent can be, for example, the simultaneous biodegradation of the microneedles with the dissolution or dispersing of the benefit agent. The rate of degradation of the needles could be controlled to allow predetermined drug-delivery rates of the benefit agent. In some embodiments, the release rate of first benefit agent could differ from that of second benefit agent. At the point in time when all of the stratum corneum piercing microneedles have degraded, film 520, 720, 820, 1520, can be removed from the site of treatment.

In some embodiments, the delivery device 10, 100, 200, 300, 500, 700, 800, 1500, may be further coated with a benefit agent, either the needles alone or in combination with the substrate.

The benefit agents may include lubricants, slip agents and the like. Alternatively, the benefit agents may provide one or more benefits to the targeted topical region. Such benefit agents may be any of a variety of compositions, including, without limitation, waxes, oils, emollients, moisturizers, and the like.

Benefit agents may include hyaluronic acid; hydroxyl acids (e.g., glycolic acid, lactic acid, malic acid, salicylic acid, citric acid, tartaric acid); anti-acne agents (e.g., salicylic acid, retinol, retinoids, or other keratolytics, and benzoyl peroxide, or other antimicrobial agents used to treat acne); shine control agents (e.g., rice protein, cotton powder, elubiol (dichlorophenyl-imidazoltioxolan); a retinoid or its derivative such as tretinoin, isotretinoin, motretinide, adapalene, tazarotene, azelaic acid, and retinol; a 5-alpha-reductase inhibitor of amino acids, e.g., glycine derivatives; hydrolyzed vegetable proteins, including soy protein and wheat protein, etc., green tea (*Camellia sinesis*) extract, and cinnamon bark extract); moisturizers; anti-microbial agents (e.g., cationic antimicrobials such as benzylkonium chloride, benzethonium chloride, triclocarbon, polyhexamethylene biguanide, cetylpyridium chloride, methyl and benzothonium chloride; salts of chlorhexidine, such as Iodopropynyl butylcarbamate, diazolidinyl urea, chlorhexidene digluconate, chlorhexidene acetate, chlorhexidine isethionate, and chlorhexidene hydrochloride; halogenated phenolic compounds, such as 2,4,4'-trichloro-2-hydroxy diphenyl ether (Triclosan); parachlorometa xylenol (PCMX); short chain alcohols, such as ethanol, propanol, and the like); antibiotics or antiseptics (mupirocin, neomycin sulfate bacitracin, polymyxin B, 1-ofloxacin, tetracyclines (chlortetracycline hydrochloride, oxytetracycline-10hydrochloride and tetracycline hydrochloride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs), anti-inflammatory agents (e.g., suitable steroidal anti-inflammatory agents such as corticosteroids such as hydrocortisone, hydroxyltriamcinolone alphamethyl dexamethasone, dexamethasonephosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinol one acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts, nonsteroidal anti-inflammatory agents, feverfew (*Tanacetum parthenium*), goji berry (*Lycium barbarum*), milk thistle extract (*Silybum marianum*), amaranth oil (*Amaranthus cruentus*), pomegranate (*Punica granatum*), yerbe mate (*Ilex paraguariensis* leaf extract), white lily flower extract (*Lilium Candidum*), olive leaf extract (*Olea europaea*) and phloretin (apple extract)); antimycotic/antifungal agents (e.g., miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs; an azole, an allylamine, or a mixture thereof); external analgesics (e.g., ibuprofen- or diclofenac; capsaicin, fentanyl, and salts thereof such fentanyl citrate; paracetamol (as acetaminophen); non-steroidal anti-inflammatory drugs (NSAIDs) such as salicylates; opioid drugs such as morphine and oxycodone; ibuprofen- or diclofenac-containing gel); antioxidants (e.g., sulfhydryl compounds and their derivatives (e.g., sodium metabisulfite and N-acetyl cysteine), lipoic acid and dihydrolipoic acid, resveratrol, lactoferrin; ascorbic acid, ascorbic acid esters, and ascorbic acid derivatives (e.g., ascorbyl palmitate and ascorbyl polypeptide); butylhydroxy anisole, butylated hydroxytoluene (butylhydroxy toluene), retinoids (e.g., retinol and retinyl palmitate), tocopherols (e.g., tocopherol acetate), tocotrienols, and ubiquinone; cysteine, N-acetylcysteine, sodium bisulfite, sodium metabisulfite, sodium formaldehydesulfoxylate, acetone sodium bisulfate, tocopherols, and nordihydroguaiaretic acid; extracts containing flavonoids and isoflavonoids and their derivatives (e.g., genistein and diadzein); extracts containing resveratrol and the like; grape seed, green tea, pine bark, and propolis; plant-derived polyphenol antioxidants such as clove, cinnamon, oregano, turmeric, cumin, parsley, basil, curry powder, mustard seed, ginger, pepper, chili powder, paprika, garlic, coriander, onion and cardamom; typical herbs such as sage, thyme, marjoram, tarragon, peppermint, oregano, savory, basil and dill weed)); depilatory agents (e.g., calcium thioglycolate or potassium thioglycolate); vitamins (e.g., Vitamin A, Vitamin B, Vitamins C, Vitamin E; either alpha, beta, gamma or delta tocopherols, niacin or niacinamide) and vitamin salts or derivatives such as ascorbic acid diglucoside and vitamin E acetate or palmitate; sunblock (e.g., titanium dioxide) and/or sunscreen (e.g., inorganic sunscreens such as titanium dioxide and zinc oxide; organic sunscreens such as octyl-methoxy cinnamates, octyl salicylate, homosalate, avobenzone); vasodilators (e.g., niacin); humectants (e.g., glycerin); anti-aging agents (e.g., retinoids; dimethylaminoathanol (DMAE), copper containing peptides); alpha hydroxy acids or fruit acids and their precursors such as glycolic acid, citric acid, lactic acid, malic acid, mandelic acid, ascorbic acid, alpha-hydroxybutyric acid, alpha-hydroxyisobutyric acid, alphahydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methyl pyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower, and salts and prodrugs thereof); carotenoids, ceramides, fatty acids, enzymes, enzyme inhibitors, minerals, steroids, peptides, amino acids, botanical extracts, colorants, allergy relief agents such as Cetirizine HCl or a pharmaceutically equivalent Cetirizine compounds, analgesic compounds such as acetaminophen, ibuprofen, ketoprofen, or pharmaceutically equivalents thereof, cough/cold relief actives such as Phenylephrine HCL, Dextromethorphan Hydrobromide Hydrate, Pseudoephedrine HCl, or pharmaceutically equivalents thereof, quit smoking medications such as Bupropion SR, Varenicline and nicotine replacement therapy agents, or pharmaceutically equivalent thereof, etc. The substances may affect the skin in any of a variety of manners, such as by moisturizing; enhancing skin tone or color (such as with pigments); treating or at least mitigating various skin conditions (such as dry or severe dry skin, eczema, psoriasis, atopic dermatitis, allergic rashes, acne, blackheads, pustules, comedones, rosacea, shingles, wrinkles, cold sores, herpes, corns, warts, sunburn, insect bites, poison ivy, etc.); applying a mechanical force (such as shrinkage) to smooth wrinkles; or, more generally, treating or mitigating the symptoms and appearance of undesired skin imperfections (such as under eye dark circle, redness of acne, fine lines and wrinkles, post inflammatory hyperpigmentation (PIH), redness, inflammation, cellulite, wrinkles, age spots, mottled pigmentation, dark spots, liver spots, under eye puffiness); removing unwanted facial or body hair; aiding in wound healing; etc. For instance, lotions, creams, oils, and even masks may be applied to skin to treat or otherwise to affect the skin. Such personal or consumer healthcare substances are absorbed into the skin generally following the principles of diffusion, under which the rate of diffusion or transport across the skin is correlated with the difference in active concentration on both sides of the skin.

The benefit agent(s) can be introduced into the reservoir (s) as a single compound, especially those that are liquid at processing and delivery temperatures. They can also be formulated into solutions, suspensions, and the like. Those benefit agents that are for therapeutic treatment of patients must be formulated with pharmaceutically acceptable carriers, such as organic solvents such ethanol, dimethyl sulfoxide ("DMSO") or dimethylformamide ("DMF"), and can be diluted preferably in aqueous solution.

As mentioned earlier, the micromachining or microcasting process for producing delivery devices are limited to producing arrays of a single composition. In the present invention, the personalized treatment uses stratum corneum piercing stratum corneum piercing microneedles with more than one benefit agent. So, the micromachining or microcasting process cannot be used.

The delivery devices of the present invention can be produced using Additive Manufacturing technology. Additive Manufacturing is a group of techniques used to quickly fabricate a physical part or assembly using three-dimensional computer aided design (CAD) data. Construction of the part or assembly is usually done using "additive layer manufacturing" technologies such as 3D printing. Additive manufacturing is a simple, effective, and economically method of making delivery devices which simultaneously delivering more than one benefit agent.

In general, the computer-aided-design-computer-aided manufacturing CAD-CAM workflow is the traditional additive manufacturing process. The process starts with the creation of geometric data, either as a 3D solid using a CAD workstation, or 2D slices using a scanning device. For Additive Manufacturing, this data must represent a valid geometric model; namely, one whose boundary surfaces enclose a finite volume, contains no holes exposing the interior unless they are designed into the structure, and do not fold back on themselves. In other words, the object must have an "inside." The model is valid if for each point in 3D space the algorithm can determine uniquely whether that point lies inside, on, or outside the boundary surface of the model. CAD post-processors will approximate the internal CAD geometric forms with a simplified mathematical form, which in turn is expressed in a specified data format which is a common feature in Additive Manufacturing. To obtain the necessary motion control trajectories to drive the Additive Manufacturing mechanism, the prepared geometric model is typically sliced into layers, and the slices are scanned into lines (producing a "2D drawing" used to generate trajectory as in computer numerical control toolpath), resulting in a layer-to-layer physical building process.

The 3D printing process enables the creation of different sizes and shapes microneedles, as well as the ability to produce delivery devices with more than one benefit agent. The location, sharpness, cavitation, and material within individual microneedles can be much more easily controlled with 3D printing than micromachining or microcasting. Soft materials, hard materials, and even liquids can be incorporated into individual microneedles. A change in delivery profile can be designed into the system to make a smart delivery device. Incompatible compounds may also be built into different sections of the delivery device without cross contamination fears.

The microneedles need to deliver active/drug at least 100 microns or deeper, but can be designed to have a variable penetration at or above 20 microns. Different applications and uses would need differing levels of penetration, solubility and design features (size, shape, angle, solubility, etc.). In some cases, the benefit agent may be dissolved into the needle material, whereas in others it may be stored in a reservoir and delivered through a microfluidic channel. In some embodiments, the benefit agent may be coated onto the needle material.

The resulting delivery device comprising a benefit agent can be use by applying to the skin in any known manner. In the event that the delivery device comprises a reservoir having an inlet port, the reservoir can be filled with a liquid comprising a benefit agent through the inlet port. The inlet port can then be closed for use, as above.

In embodiments in which multiple benefit agents are to be delivered, at least two independent liquid systems, each including a fillable reservoir having an inlet port and coupled to at least one microfluidic channel associated with at least one microneedle, can be filled through their respective inlet ports with a desired liquid comprising a benefit agent. The inlet ports can be closed for use, as above.

In some embodiments, these dermal delivery devices, or patches, can include sensors which detect the amount of a liquid delivered over time, so that the amount of drug can be monitored using an App so that consumers (users) can track the amount that is delivered over a period of time and can change the drug delivery profile as desired.

In some embodiments, a large bolus of the benefit agents can be delivered by these dermal delivery devices by preparing water soluble microneedles with high concentration of benefit agents; or by preparing coated microneedles with high concentration of benefit agents. The delivery of low concentration of benefit agents from the reservoir can then provide longer term delivery of the benefit agents.

The present invention will be further understood by reference to the following specific Examples which are illustrative of the composition, form and method of producing the present invention. It is to be understood that many variations of composition, form and method of producing this would be apparent to those skilled in the art. The following Examples, wherein parts and percentages are by weight unless otherwise indicated, are only illustrative.

EXAMPLES

Example 1: Transdermal Drug Delivery Devices for Long Duration Allergy Relief Applications A transdermal drug delivery devices in the form of a film having with an internal liquid reservoir(s) and microfluidic channel as well as microneedles for use in allergy relief applications can be prepared as follows.

Cetirizine HCl, an antihistamine used to relieve allergy symptoms such as watery eyes, runny nose, itching eyes/nose, sneezing, hives, and itching, can be dissolved in organic solvents such as DMSO and DMF and can be diluted preferably in aqueous solution. The Cetirizine HCl may be stored in the internal liquid reservoir(s) and delivered through a microfluidic channel to the hollow microneedles for transdermal delivery.

The amount of Cetirizine will depend on the duration for delivery of the drug. For a seven-day Cetirizine patch, for example, at least about 70 mg to about 100 mg of drug will be required to be stored in the reservoir(s) and delivered through hollow microneedles over a period of seven days. The length and thickness of the hollow microneedles can range from about 100 microns to about 0.5 mm.

Since Cetirizine HCl is highly water soluble, there will be some loss during the transport of drug through the skin and therefore more than 70 mg of drug could be required to compensate for drug loss.

Other antihistamines, such as diphenhydramine, can also be used for this application. The amount of drug will range from about 700 to about 1000 mg for a seven-day drug delivery device.

Example 2: Transdermal Drug Delivery Devices for Long Duration Cough/Cold Relief Applications Transdermal drug delivery devices in the form of a film having with an internal liquid reservoir(s) and microfluidic channel as well as microneedles for use in cough/cold relief applications can be prepared as follows.
  (a) Phenylephrine HCL, a decongestant used to relieve stuffiness from colds can be dissolved in organic solvents such ethanol, DMSO or DMF, and can be diluted preferably in aqueous solution. The Phenylephrine HCL may be stored in the internal liquid reservoir(s) and delivered through a microfluidic channel to the hollow microneedles for transdermal delivery.
    The amount of Phenylephrine will depend on the duration for delivery of the active. For a seven-day patch, for example, about 160 mg to about 200 mg of drug will be required to be stored in the reservoir(s) and delivered through hollow microneedles over a period of seven days. The length and thickness of the hollow microneedles can range from about 100 microns to about 0.5 mm.
  (b) Dextromethorphan Hydrobromide Hydrate used for temporary relief of coughs without phlegm that are caused by certain infections of the air passages can be dissolved in organic solvents such ethanol, DMSO or DMF, and can be diluted preferably in aqueous solution. The Dextromethorphan Hydrobromide Hydrate may be stored in the internal liquid reservoir(s) and delivered through a microfluidic channel to the hollow microneedles for transdermal delivery.
    The amount of Dextromethorphan Hydrobromide Hydrate will depend on the duration for delivery of the active. For a seven-day patch, for example, about 90 mg to about 120 mg of the drug will need to be stored in the reservoir and delivered through hollow microneedles over a period of seven days. The length and thickness of the hollow microneedles can range from about 100 microns to about 0.5 mm.
  (c) Pseudoephedrine HCl used for the temporary relief of stuffy nose and sinus pain/pressure caused by infection can be dissolved in organic solvents such ethanol, DMSO or DMF, and can be diluted preferably in aqueous solution. The Pseudoephedrine HCl may be stored in the internal liquid reservoir(s) and delivered through a microfluidic channel to the hollow microneedles for transdermal delivery.
    The amount of Pseudoephedrine HCl will depend on the duration for delivery of the active. For a seven-day patch, for example, about 1500 mg to about 1700 mg of the drug will need to be stored in the reservoir and delivered through hollow microneedles over a period of seven days. The length and thickness of the hollow microneedles can range from about 100 microns to about 0.5 mm.

Example 3: Transdermal Drug Delivery Devices for Long Duration Pain Relief Applications The most commonly used drugs for pain can include acetaminophen, ibuprofen, naproxen and ketoprofen. These actives may be stored in the internal liquid reservoir(s) and delivered through a microfluidic channel to the hollow microneedles for transdermal delivery. For an acetaminophen patch, the drug amount will depend on the duration and will range from about 1300 to about 10,000 mg of drug for one-day to seven-day patches, respectively. The length and thickness of the hollow microneedles can range from about 250 microns to about 0.5 mm as the amount of drug required to initiate the benefits is larger.

For an ibuprofen patch, the amount of drug will range from about 600 mg to about 4000 mg for a one-day to seven-day patches, respectively. The length and thickness of the hollow microneedles can range from about 100 microns to about 0.5 mm.

The most preferred drug for pain application can be ketoprofen as the amount of drug required is lower compared to the other pain relieving actives. For a one-day patch the drug can be about 40 mg and can go as high as about 300 mg for a seven-day patch. The length and thickness of the hollow microneedles can range from about 100 microns to about 0.5 mm.

Example 4: Transdermal Drug Delivery Devices for Long Duration Applications for Using Combined Drugs Two drugs can be combined to provide improved cough/cold relief for consumers. Solutions of Phenylephrine HCL and Dextromethorphan Hydrobromide Hydrate can be prepared and kept separate in different microchannels or reservoirs to prevent interaction between the drugs. Individual drugs can be delivered through microneedles separately and the ratio between the drugs can be altered based on the consumer needs. Other drugs can also be included for pain and cough/cold applications, and these drugs can be delivered separately to minimize interaction between drugs and the dosing can be monitored.

In some embodiments, these patches can include sensors so that the amount of drug can be monitored using an App so that consumers can track the amount that is delivered over a period of time and can change the drug delivery profile as desired.

What is claimed is:

1. A transdermal delivery device for long duration delivery of at least two active formulations comprising:
  (a) a film having first and second outwardly facing major surfaces;

(b) a first active formulation subsystem comprising:
  (i) at least one first active formulation liquid reservoir containing a first active formulation disposed within the film;
  (ii) at least one first active formulation microfluidic channel having a major transverse dimension between about 100 nm and 0.5 mm disposed within the film and in fluid communication with the at least one first active formulation liquid reservoir;
  (iii) at least one first active formulation outlet port operatively connected to the first outwardly facing major surface of the film in fluid communication with the at least one first active formulation microfluidic channel; and
  (iv) at least one first active formulation microneedle in fluid communication with the at least one first active formulation outlet port; and
(c) a second active formulation subsystem comprising:
  (i) at least one second active formulation liquid reservoir containing a second active formulation disposed within the film;
  (ii) at least one second active formulation microfluidic channel having a major transverse dimension between about 100 nm and 0.5 mm disposed within the film and in fluid communication with the at least one second active formulation liquid reservoir;
  (iii) at least one second active formulation outlet port operatively connected to the first outwardly facing major surface of the film in fluid communication with the at least one second active formulation microfluidic channel; and
  (iv) at least one second active formulation microneedle in fluid communication with the at least one second active formulation outlet port; and
(d) an array of outlet ports comprising at least one first set of outlet ports being operatively connected to the first outwardly facing major surface of the film in fluid communication with the at least one first microfluidic channel and at least one second set of outlet ports being operatively connected to the first outwardly facing major surface of the film in fluid communication with the at least one second microfluidic channel, wherein at least one outlet port of the first set of outlet ports is disposed among the second set of outlet ports.

2. The transdermal delivery device of claim 1, further comprising a sensor.

3. The transdermal delivery device of claim 2, wherein the sensor detects an amount of a liquid delivered over time.

4. The transdermal delivery device of claim 1, wherein the first active formulation comprises a solution of Phenylephrine HCl or a pharmaceutically equivalent Phenylephrine compound in a pharmaceutically acceptable solvent.

5. The transdermal delivery device of claim 4, comprising a total amount of Phenylephrine HCl or a pharmaceutically equivalent Phenylephrine compound of between about 160 mg and about 200 mg.

6. The transdermal delivery device of claim 1, wherein the second active formulation comprises a solution of Dextromethorphan Hydrobromide Hydrate or a pharmaceutically acceptable Dextromethorphan compound in a pharmaceutically acceptable solvent.

7. The transdermal delivery device of claim 6, comprising a total amount of Dextromethorphan Hydrobromide Hydrate or a pharmaceutically equivalent Dextromethorphan compound of between about 90 mg and about 120 mg.

8. The transdermal delivery device of claim 1, further comprising:

(e) a third active formulation subsystem comprising:
  (i) at least one third active formulation liquid reservoir containing a third active formulation disposed within the film;
  (ii) at least one third active formulation microfluidic channel having a major transverse dimension between about 100 nm and 0.5 mm disposed within the film and in fluid communication with the at least one third active formulation liquid reservoir;
  (iii) at least one third active formulation outlet port operatively connected to the first outwardly facing major surface of the film in fluid communication with the at least one third active formulation microfluidic channel; and
  (iv) at least one third active formulation microneedle in fluid communication with the at least one third active formulation outlet port.

9. The transdermal delivery device of claim 8, wherein the third active formulation comprises a solution of Pseudoephedrine HCl or a pharmaceutically equivalent Pseudoephedrine compound in a pharmaceutically acceptable solvent.

10. The transdermal delivery device of claim 9, comprising a total amount of Pseudoephedrine HCl or a pharmaceutically equivalent Pseudoephedrine compound of between about 1500 mg and about 1700 mg.

11. A method of producing delivery devices comprising the steps of:
(a) forming a transdermal delivery device via additive manufacturing, the transdermal delivery device comprising:
  (i) a film having first and second outwardly facing major surfaces and a sensor;
  (ii) a first active formulation subsystem comprising:
    (A) at least one first active formulation liquid reservoir disposed within the film and having an inlet port;
    (B) at least one first active formulation microfluidic channel having a major transverse dimension between about 100 nm and 0.5 mm disposed within the film and in fluid communication with the at least one first active formulation liquid reservoir;
    (C) at least one first active formulation outlet port operatively connected to the first outwardly facing major surface of the film in fluid communication with the at least one first active formulation microfluidic channel;
    (D) at least one first active formulation microneedle in fluid communication with the at least one first active formulation outlet port; and
  (iii) a second active formulation subsystem comprising:
    (A) at least one second active formulation liquid reservoir disposed within the film and having an inlet port;
    (B) at least one second active formulation microfluidic channel having a major transverse dimension between about 100 nm and 0.5 mm disposed within the film and in fluid communication with the at least one second active formulation liquid reservoir;
    (C) at least one second active formulation outlet port operatively connected to the first outwardly facing major surface of the film in fluid communication with the at least one second active formulation microfluidic channel; and (D) at least one second active formulation microneedle in fluid communication with the at least one second active formulation outlet port; and (iv) an array of outlet ports comprising at least one first set of outlet ports being operatively connected to the first outwardly facing major surface of the film in fluid communication with the at least one first microfluidic channel and at least one second set of outlet ports being operatively connected to the first outwardly facing major surface of the film in fluid communication with the at least one second microfluidic channel, wherein at least one outlet port of the first set of outlet ports is disposed among the second set of outlet ports; and (b) filling the at least one first active formulation liquid reservoir with a liquid comprising a first benefit agent through the first active formulation inlet port; and (c) filling the at least one second active formulation liquid reservoir with a liquid comprising a second benefit agent through the second active formulation inlet port; and (d) closing the active formulation inlet ports.

12. The method of claim 11, further comprising sensing an amount of liquid delivered over time.

13. The method of claim 11, wherein the first benefit agent comprises solution of Phenylephrine HCl or a pharmaceutically equivalent Phenylephrine compound in a pharmaceutically acceptable solvent.

14. The method of claim 11, wherein the second benefit agent comprises solution of Dextromethorphan Hydrobromide Hydrate or a pharmaceutically equivalent Dextromethorphan compound in a pharmaceutically acceptable solvent.

15. The method of claim 11, wherein the transdermal delivery device further comprises:

(v) a third active formulation subsystem comprising:

(A) at least one third active formulation liquid reservoir disposed within the film and having an inlet port;

(B) at least one third active formulation microfluidic channel having a major transverse dimension between about 100 nm and 0.5 mm disposed within the film and in fluid communication with the at least one third active formulation liquid reservoir;

(C) at least one third active formulation outlet port operatively connected to the first outwardly facing major surface of the film in fluid communication with the at least one third active formulation microfluidic channel; and (D) at least one third active formulation microneedle in fluid communication with the at least one third active formulation outlet port;

and wherein the process further includes:

(e) filling the at least one third active formulation liquid reservoir with a liquid comprising a third benefit agent through the third active formulation inlet port.

16. The method of claim 15, wherein the third benefit agent comprises solution of Pseudoephedrine HCl or a pharmaceutically equivalent Pseudoephedrine compound in a pharmaceutically acceptable solvent.

* * * * *